US010595952B2

(12) United States Patent
Forrest et al.

(10) Patent No.: US 10,595,952 B2
(45) Date of Patent: Mar. 24, 2020

(54) PROCESS AND APPARATUS FOR MANAGING MEDICAL DEVICE SELECTION AND IMPLANTATION

(71) Applicant: Vector Medical, LLC, Pineville, LA (US)

(72) Inventors: Daniel H. Forrest, Alexandria, LA (US); Vinod Dasa, New Orleans, LA (US); Kenneth Douglas Burnette, Pineville, LA (US); W. Brent Pearson, Alexandria, LA (US); Christopher J. Rich, Alexandria, LA (US); Albert Hernandez, Chino Hills, CA (US)

(73) Assignee: Sight Medical, LLC, Alexandria, LA (US)

( * ) Notice: Subject to any disclaimer, the term of this patent is extended or adjusted under 35 U.S.C. 154(b) by 574 days.

(21) Appl. No.: 14/984,868

(22) Filed: Dec. 30, 2015

(65) Prior Publication Data

US 2016/0220323 A1  Aug. 4, 2016

Related U.S. Application Data

(60) Provisional application No. 62/098,877, filed on Dec. 31, 2014.

(51) Int. Cl.
*A61B 34/10* (2016.01)
*A61B 50/18* (2016.01)
(Continued)

(52) U.S. Cl.
CPC .............. *A61B 50/18* (2016.02); *A61B 17/16* (2013.01); *A61B 17/88* (2013.01); *A61B 34/10* (2016.02);
(Continued)

(58) Field of Classification Search
CPC .. A61L 334/10; A61B 34/10; A61B 2034/252
See application file for complete search history.

(56) References Cited

U.S. PATENT DOCUMENTS 8,707,963 B2 * 4/2014 Davis ..................... A61F 2/30
128/898
9,050,063 B2 * 6/2015 Roe ....................... G06F 19/324
(Continued)

OTHER PUBLICATIONS

PCT Application No. US2015/068152; International Search Report and Written Opinion of the International Searching Authority for Applicant Vector Medical, LLC dated May 17, 2016.
(Continued)

*Primary Examiner* — Mark A Connolly
(74) *Attorney, Agent, or Firm* — Jones Walker LLP

(57) ABSTRACT

A method of selecting an instrument set for an orthopedic implant procedure. The method utilizes a computer programmed with a data structure configured to store (i) a set of implant components and implant instruments; and (ii) a set of surgical instruments utilized in performing the procedure. The method selects a sub-set of implant components and implant instruments based upon a determination of component types and then selects a sub-set of surgical instruments based upon a determination of surgical techniques. The method arranges the sub-set of surgical instruments and implant instruments into a substantially specific order based upon a determination of a sequence of bone cuts to be performed in the procedure.

7 Claims, 37 Drawing Sheets

(51) Int. Cl.
*G06Q 50/22* (2018.01)
*G16H 20/40* (2018.01)
*A61B 34/00* (2016.01)
*A61B 17/16* (2006.01)
*A61B 17/88* (2006.01)
*G05B 15/02* (2006.01)

(52) U.S. Cl.
CPC .............. *A61B 34/25* (2016.02); *G05B 15/02* (2013.01); *G06Q 50/22* (2013.01); *G16H 20/40* (2018.01); *A61B 2034/108* (2016.02); *A61B 2034/252* (2016.02)

(56) References Cited

U.S. PATENT DOCUMENTS

| | | | |
|---|---|---|---|
| 9,351,798 B2 | 5/2016 | Roe et al. | |
| 2006/0190130 A1* | 8/2006 | Fedor | G06M 7/04 700/236 |
| 2008/0059228 A1* | 3/2008 | Bossi | G06F 19/3418 705/2 |
| 2008/0270341 A1* | 10/2008 | Youngblood | A61B 34/25 |
| 2012/0316987 A1* | 12/2012 | DeBusk | G06Q 10/08 705/26.8 |
| 2013/0166254 A1* | 6/2013 | Grimm | A61B 34/10 703/1 |
| 2013/0300075 A1* | 11/2013 | Arceta | A61G 12/001 280/33.991 |
| 2014/0249515 A1 | 9/2014 | Martin | |
| 2014/0263633 A1* | 9/2014 | Schmucker | G06Q 10/0875 235/385 |
| 2016/0045276 A1 | 2/2016 | Pfanner et al. | |
| 2016/0055765 A1* | 2/2016 | Monaghan | G09B 23/28 434/429 |

OTHER PUBLICATIONS

PCT Application No. US2015/068152; International Preliminary Report on Patentability for Applicant Vector Medical, LLC dated May 30, 2017.

Lalys, Florent, and Pierre Jannin. "Surgical process modelling: a review." International journal of computer assisted radiology and surgery 9.3 (2014): 495-511, first published online: Sep. 8, 2013.

Zimmer NexGen CR-Flex and LPS-Flex Knees Brochure, "Surgical Technique with Posterior Referencing Instrumentation" At least as early as 2011.

* cited by examiner

Identify Key Anatomical Points

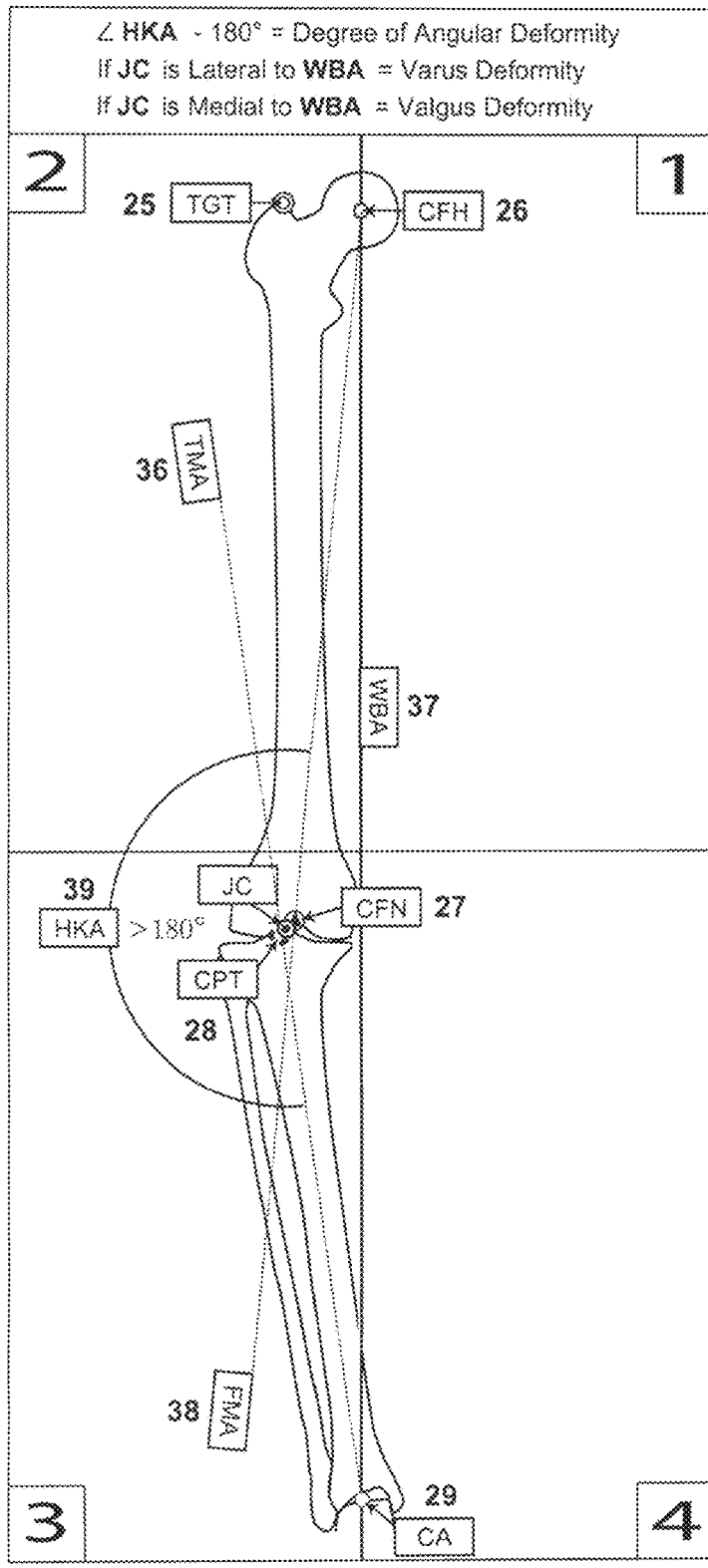
User-guided System
FIG. 4
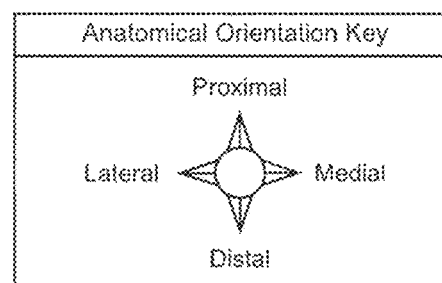
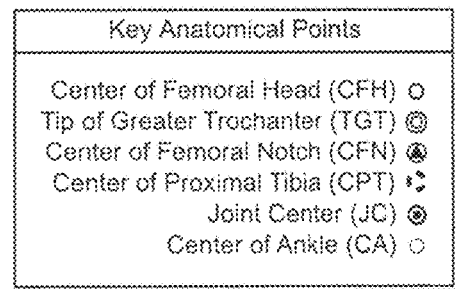
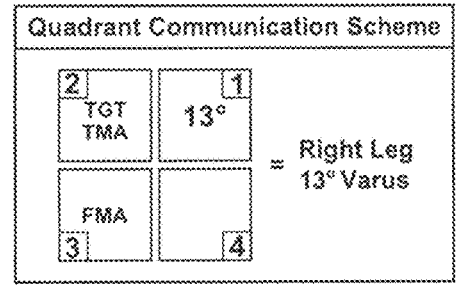

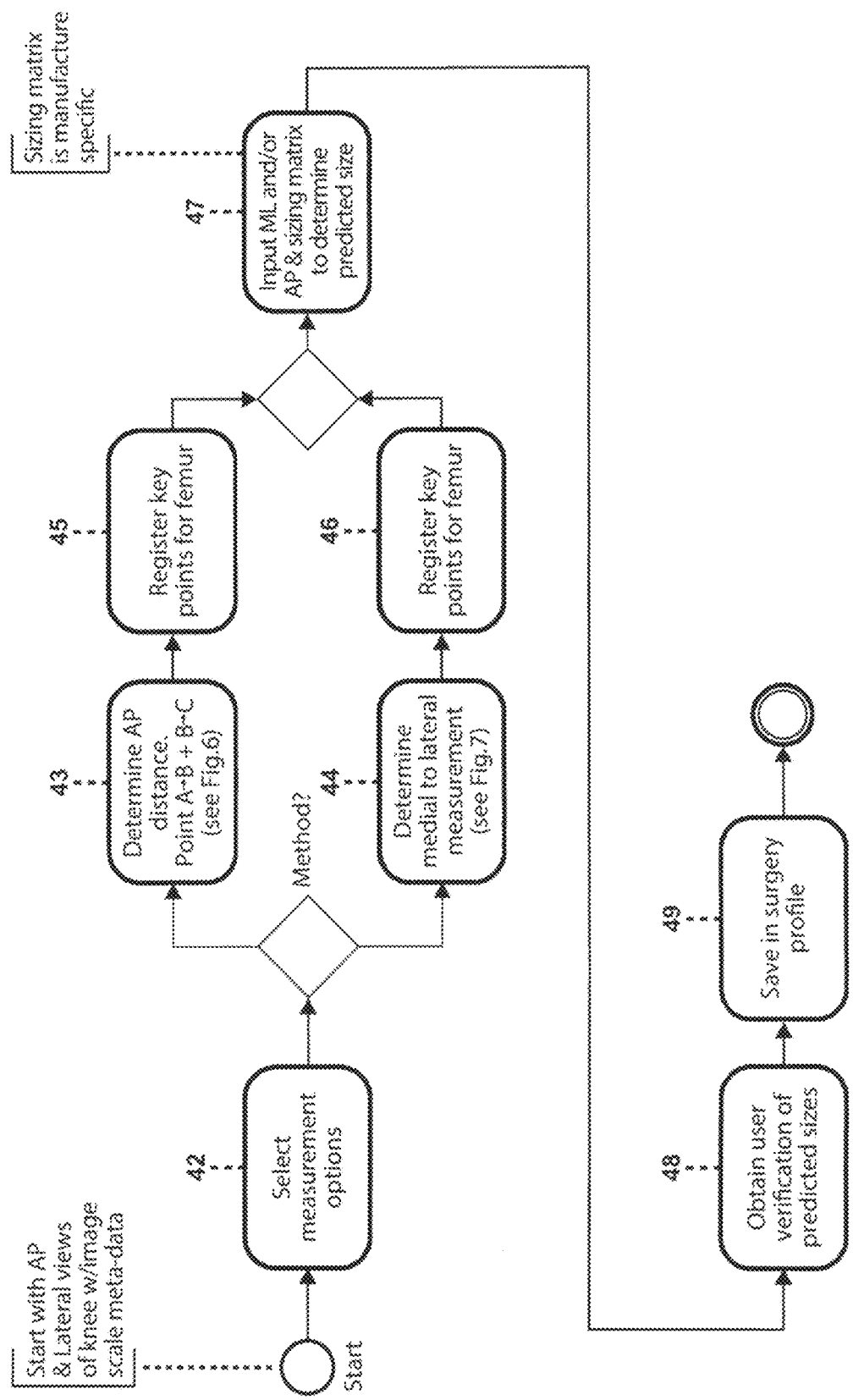

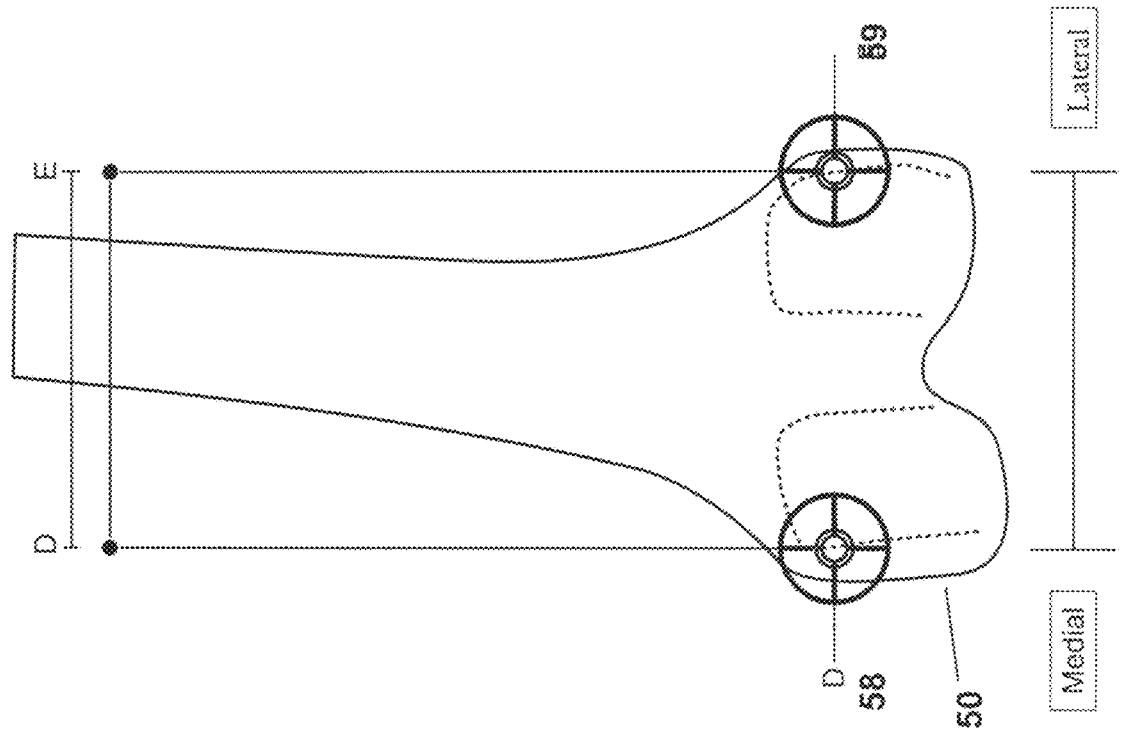
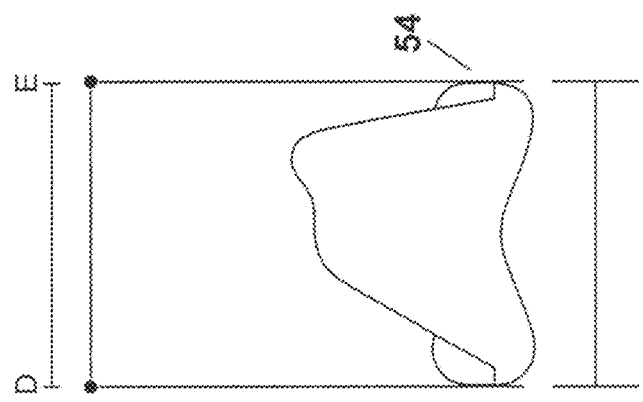
FIG. 7A  FIG. 7B  FIG. 7C
D = Medial posterior condyle border
E = Lateral posterior condyle border
| Size | ML |
|------|----|
| 1 | 56 |
| 2 | 60 |
| 3 | 64 |
| 4 | 68 |
| 5 | 72 |
| 6 | 76 |
| 7 | 80 |

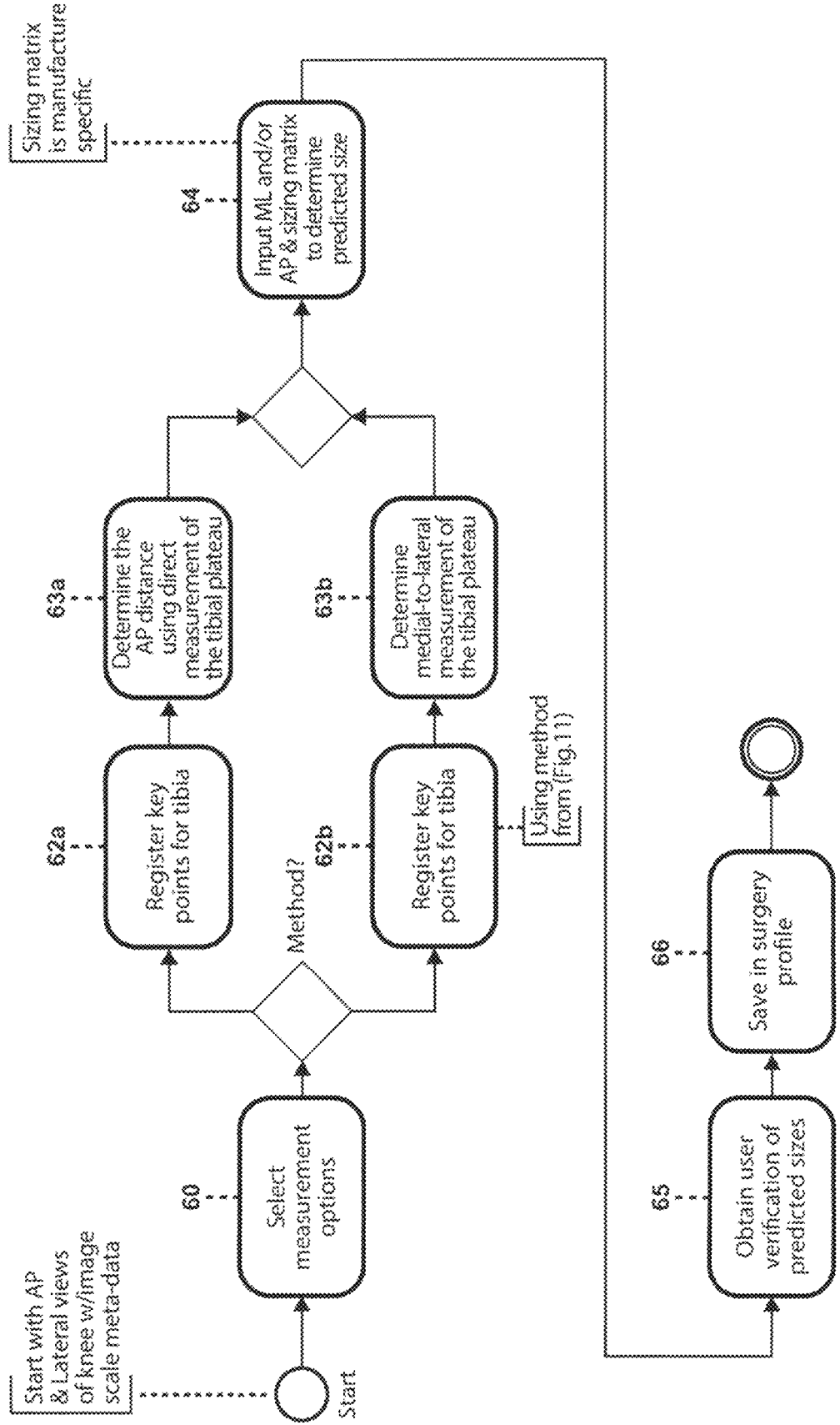

| Size | ML |
|---|---|
| 1 | 63 |
| 2 | 66 |
| 3 | 69 |
| 4 | 72 |
| 5 | 76 |
| 6 | 80 |
| 7 | 84 |

Patient Profile

Patient Profile

Patient Profile

Surgeon Profile

Surgeon Profile

Surgery Profile

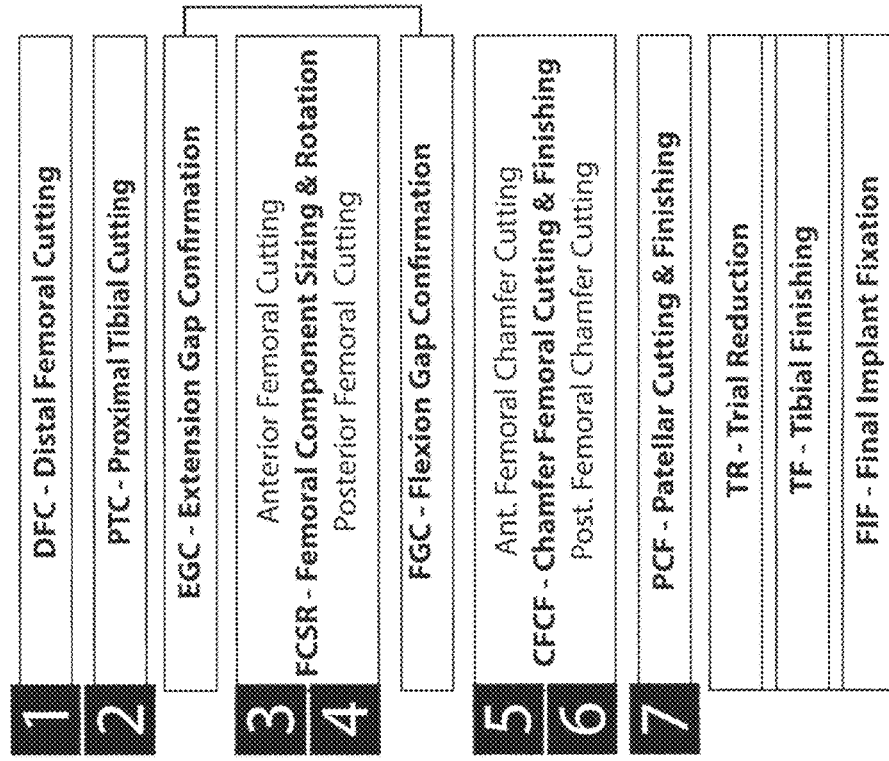

FIG. 15B

Patient Profile

Femoral Component Type: Posterior Stabilized
Femoral Component Fixation Type: Cemented
Tibial Component Modularity: Modular metal-back
Tibial Baseplate Comp Fixation Type: Cemented
Tibial Component Bearing Surface Design: Standard
Patellar Component Type: Onset

Surgeon Profile

Joint Balancing Technique: Measured Resection
Femoral Alignment Technique: Intramedullary
Tibial Alignment Technique: Extramedullary
Patella Resurfacing Technique: Resection Guide

Surgery Profile

1 = Distal Femoral Cut
2 = Proximal Tibial Cut
3 = Anterior Femoral Cut
4 = Posterior Femoral Cut
5 = Anterior Femoral Chamfer Cut
6 = Posterior Femoral Chamfer Cut
7 = Patella Cut

FIG. 15A

Items Automatically Reduced, Grouped, & Sorted

| process | instrGrp | keySeq | tableOfContents | activity |
|---|---|---|---|---|
| step 1 | DFC | cut1 | Fig.16A | femAlignment |
| step 2 | | | | distalFemCutting |
| step 3 | PTC | cut2 | Fig.16B | tibAlignment |
| step 4 | | | | proxTibCutting |
| step 5 | EGC | gapCk1 | Fig.16C | gapCheck&Balancing |
| step 6 | FCSR | cut3 | Fig.16D | femCompPlanning |
| step 7 | | cut4 | | antFemCutting |
| step 8 | | | | postFemCutting |
| step 9 | FGC | gapCk2 | Fig.16E | gapCheck&Balancing |
| step 10 | CFCF | cut5 | Fig.16F | antChamferFemCutting |
| step 11 | | cut6 | | postChamferFemCuttin |
| step 12 | | | | femFinishing |
| step 13 | PCF | cut7 | Fig.16G | patResurfaceCutting |
| step 14 | | | | patFinishing |
| step 15 | TR | trial1 | Fig.16.H | patTrialing |
| step 16 | | trial2 | | femTrialing |
| step 17 | | trial3 | | tibTrialing |
| step 18 | TF | tibKeel | Fig16.I | tibBasefinishing |
| step 20 | FIF | imp1 | Fig16.J | femCompImplantation |
| step 21 | | imp2 | | tibBaseplateImplatation |
| step 22 | | imp3 | | patCompImplantation |
| step 23 | | imp4 | | tibInsertImplantation |

FIG. 15C

| process | instrGrp | keySeq | tableOfContents | activity |
|---|---|---|---|---|
| step 1 | DFC | cut1 | Fig.16A | femAlignment |

| Description | Qty | Image |
|---|---|---|
| T-handle | 1 | 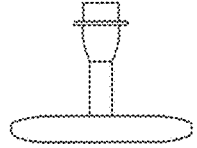 |
| Femoral IM alignment rod | 1 |  |
| Femoral drill | 1 |  |
| Femoral IM alignment guide | 1 |  |
| Anchoring pins | 2 |  |

| process | instrGrp | keySeq | tableOfContents | activity |
|---|---|---|---|---|
| step 2 | DFC | cut1 | Fig.16A | distalFemCutting |

| Description | Qty | Image |
|---|---|---|
| Distal femoral alignment guide | 1 |  |
| Distal femoral cutting guide | 1 | 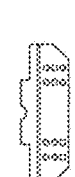 |
| Drill pins | 3 |  |

FIG. 15D

Instrument Configuration Layout #1

DFC – Distal Femoral Cutting

T-handle
Femoral drill
Femoral IM rod
Femoral IM alignment guide
Distal femoral alignment guide
Distal femoral cutting guide
Anchoring Pins
Drill Pins

PTC – Proximal Tibial Cutting

Tibial stylus
Tibial cutting guide, right
Tibial EM alignment guide
Tibial Alignment rod
Drill pins
Pin Driver

EGC – Extension Gap Confirmation

Extension gap spacer block
Spacer block alignment rod
Gap gauge, 9mm
Gap gauge, 11mm
Gap gauge, 13mm
Gap gauge, 18mm
Gap gauge, 15mm

FIG. 16C

Instrument Configuration Layout # 2

| Instructions | Materials | Instruments |

FCSR - Femoral Component Sizing & Rotation

Femoral sizing & rotation guide, sz 1-7
Ant/Post Ref, 4-n-1 cutting guide, #3
Ant/Post Ref, 4-n-1 cutting guide, #4
Ant/Post Ref, 4-n-1 cutting guide, #5
Anchoring Pins
Pin Driver

| Instructions | Materials | Instruments |

FGC - Flexion Gap Confirmation

Flexion gap spacer block
Spacer block alignment rod
Gap gauge, 9mm
Gap gauge, 11mm
Gap gauge, 13mm
Gap gauge, 18mm
Gap gauge, 15mm

FIG. 16E

| Instructions | Materials | Instruments |

CFCF - Chamfer Femoral Cutting & Finishing

Ant/Post Ref, 4-n-1 cutting guide, #3
Ant/Post Ref, 4-n-1 cutting guide, #4
Ant/Post Ref, 4-n-1 cutting guide, #5
PS Notch cutting jig, #3
PS Notch cutting jig, #4
PS Notch cutting jig, #5
PS cutting jig drill guide
PS reamer
PS housing punch
PS housing impactor
Implant Instruments
Anchoring Pins
Pin Driver
Pin Puller

| Instrument Configuration Layout # 3 | | |
| --- | --- | --- |
| Instructions | Materials | Instruments |
| PCF - Patellar Cutting & Finishing <br><br> Patella Resection Guide <br> Resection Guide <br> Patellar caliper <br> On set patellar drill guide, 32mm <br> On set patellar drill guide, 35mm <br> On set patellar drill guide, 38mm <br> On set patellar peg drill | | |

FIG. 16G

| Instructions | Materials | Instruments |
| --- | --- | --- |
| TR - Trial Reduction <br> [ Implant interchangeability confirmed ] <br><br> Fem Comp trial PS, Cemented, #3 right <br> Fem Comp trial PS, Cemented, #4 right <br> Fem Comp trial PS, Cemented, #5 right <br> Cemented, Tibial baseplate, #2 <br> Cemented, Tibial baseplate, #3 <br> Cemented, Tibial baseplate, #4 <br> Tibial insert PS, Standard, #2 × 9mm <br> Tibial insert PS, Standard, #2 × 11mm <br> Tibial insert PS, Standard, #2 × 13mm <br> Tibial insert PS, Standard, #2 × 15mm <br> Tibial insert PS, Standard, #2 × 18mm <br> Tibial insert PS, Standard, #3 × 9mm <br> Tibial insert PS, Standard, #3 × 11mm <br> Tibial insert PS, Standard, #3 × 13mm <br> Tibial insert PS, Standard, #3 × 15mm <br> Tibial insert PS, Standard, #3 × 18mm <br> Tibial insert PS, Standard, #4 × 9mm <br> Tibial insert PS, Standard, #4 × 11mm <br> Tibial insert PS, Standard, #4 × 13mm <br> Tibial insert PS, Standard, #4 × 15mm <br> Tibial insert PS, Standard, #4 × 18mm <br> Trial, on set, 32mm Patellar <br> Trial, on set, 35mm Patellar <br> Trial, on set, 38mm Patellar <br> Femoral Trial Component Driver <br> Tibial Insert Trial Component Impactor <br> Tibial Insert Trial Component Extractor | | |

FIG. 16H

| Instructions | Materials | Instruments |
| --- | --- | --- |
| TF - Tibial Finishing <br><br> Cemented tibial punch handle <br> Cemented tibia punch, S <br> Cemented tibia punch, M <br> Cemented, Tibial baseplate, #2 <br> Cemented, Tibial baseplate, #3 <br> Cemented, Tibial baseplate, #4 <br> Tibial drill <br> Tibial drill guide <br> Anchoring pins <br> Pin Driver <br> Pin Puller | | |

FIG. 16I

| System Name | Version | Set # |
|---|---|---|
| Tray Name | Format | Weight Tray # |
| Mfg Ref # | | VIN # |

251

| ODOC Assignment | Table of Contents | OR Setup Diagram |
|---|---|---|
| 252 | 253 | 254 |

Instrument Configuration Layout # 4

Instructions | Materials | Instruments

FIF - Final Implant Fixation

Femoral Implant Impactor
Tibial Baseplate Implant Impactor
Tibial Insert Implant Impactor
Patella Implant Clamp Final Implant Components →

Femoral Component
Tibia Baseplate
Tibial Insert
Patellar Component

FIG. 16J

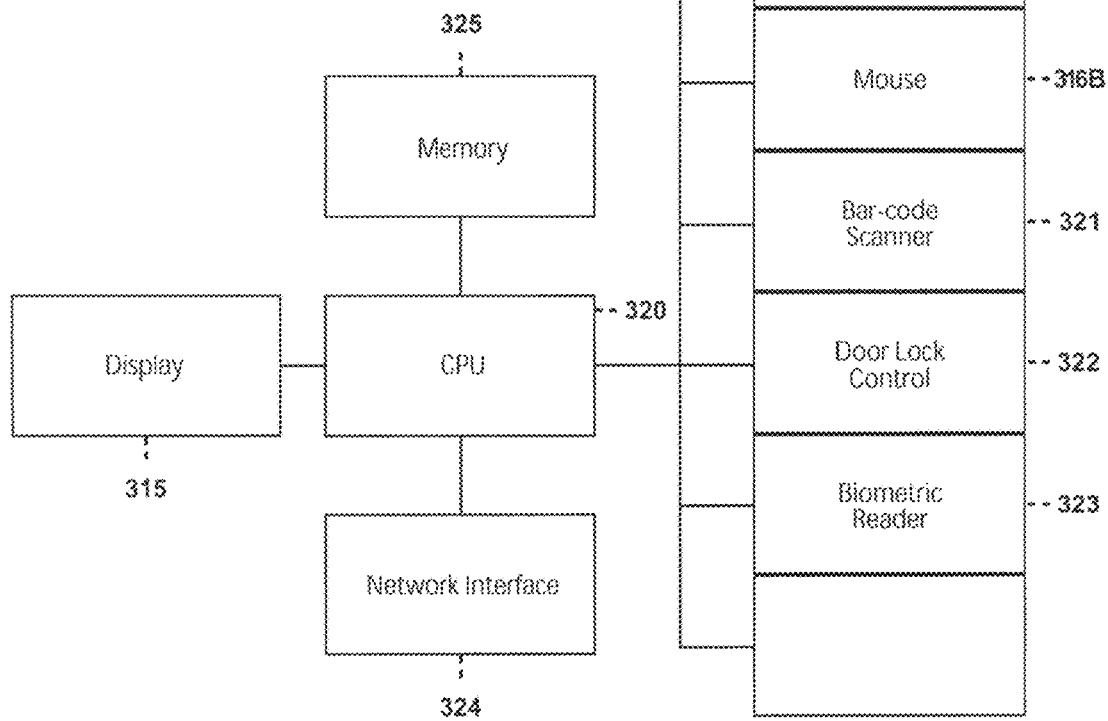
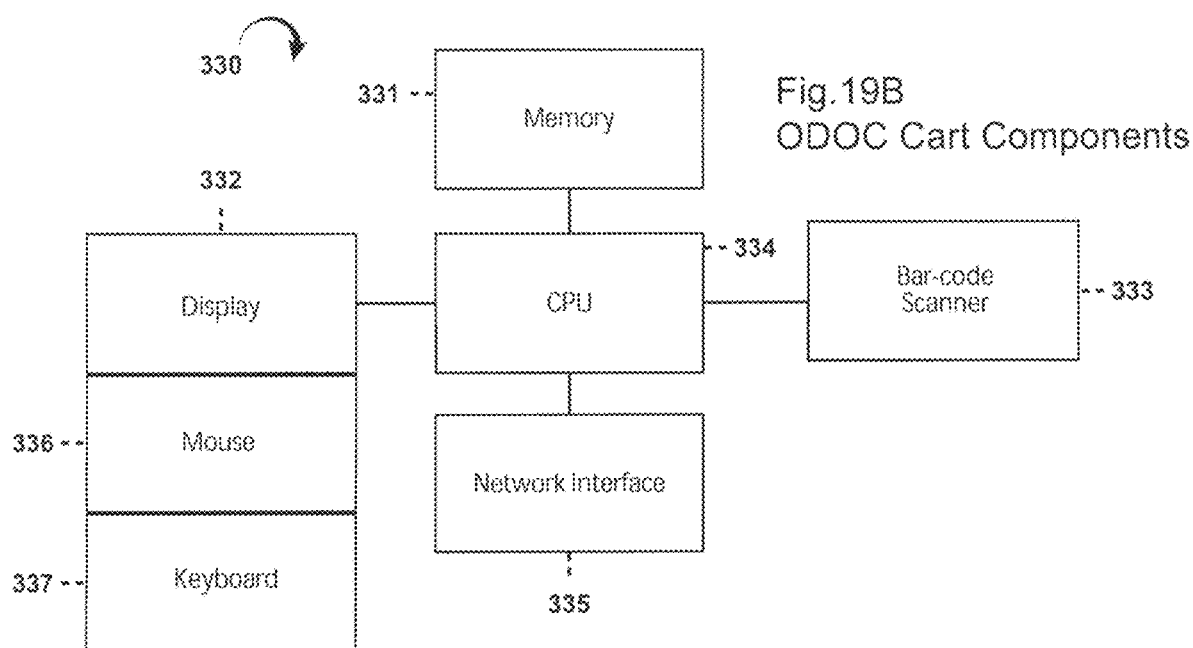

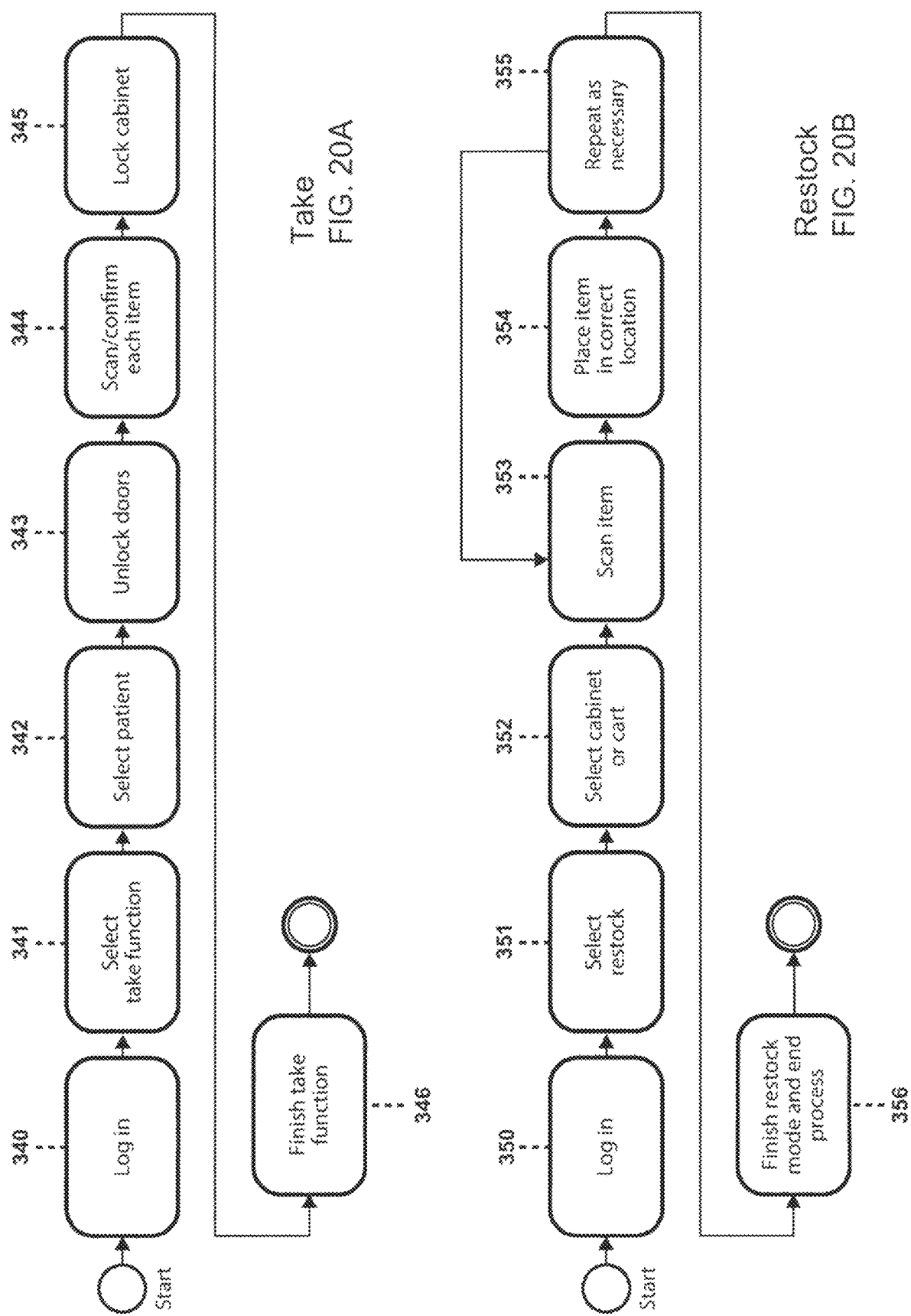

Transfer

Top Level Workflow

Add Inventory To Cabinet

Verify Inventory Prior To Surgery

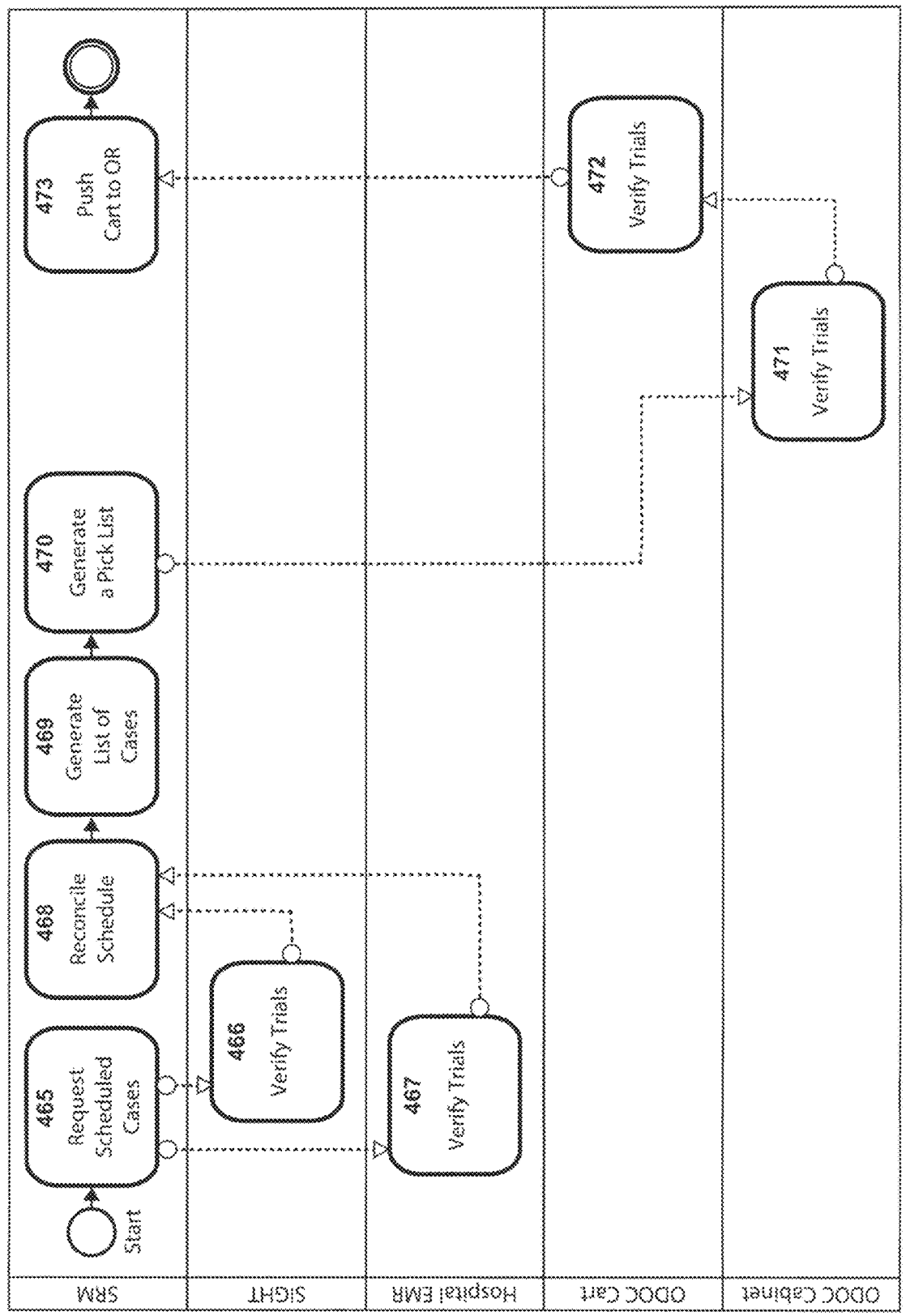
FIG. 26 - Transfer Inventory To ODOC Deployment Cart

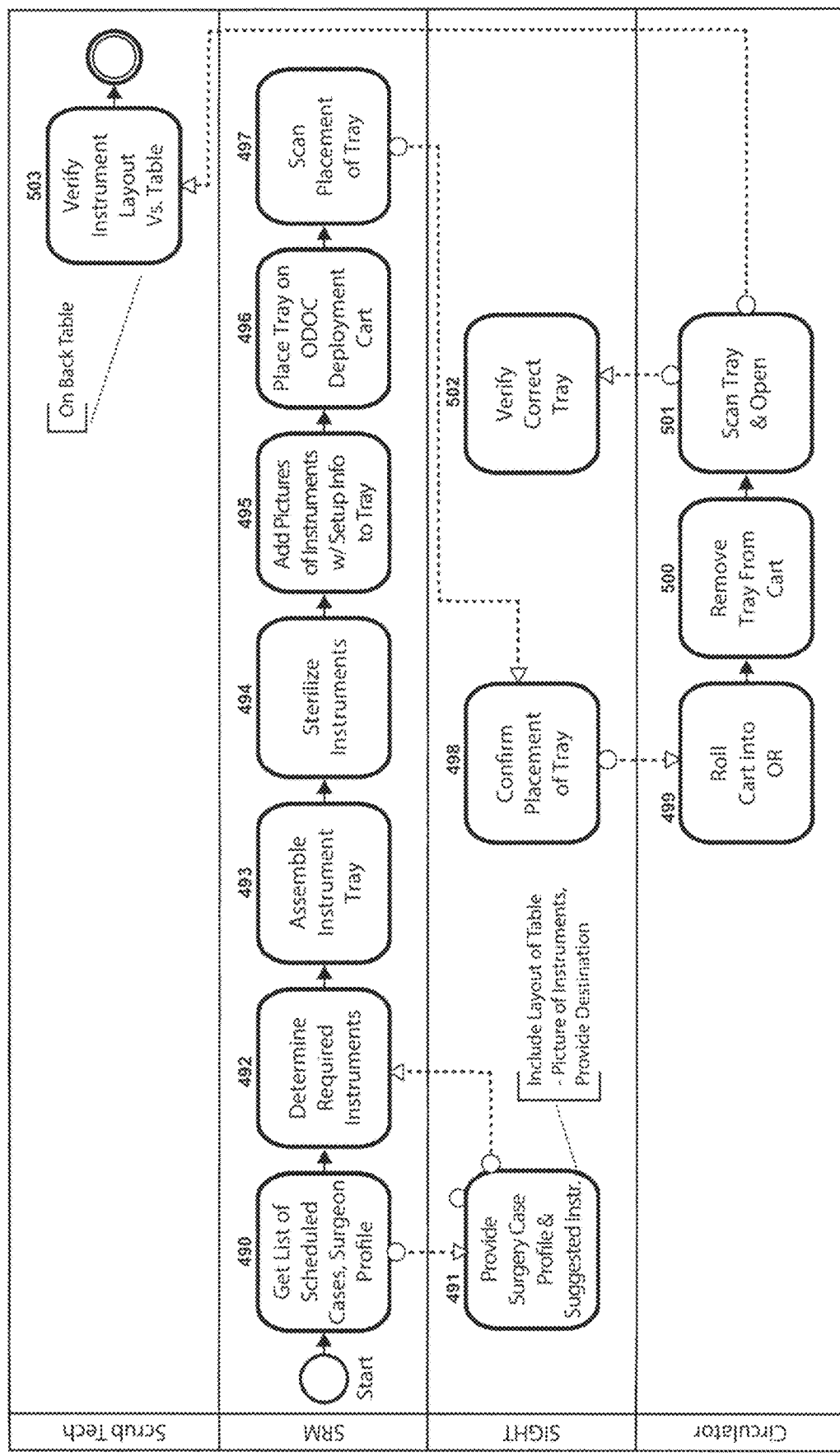

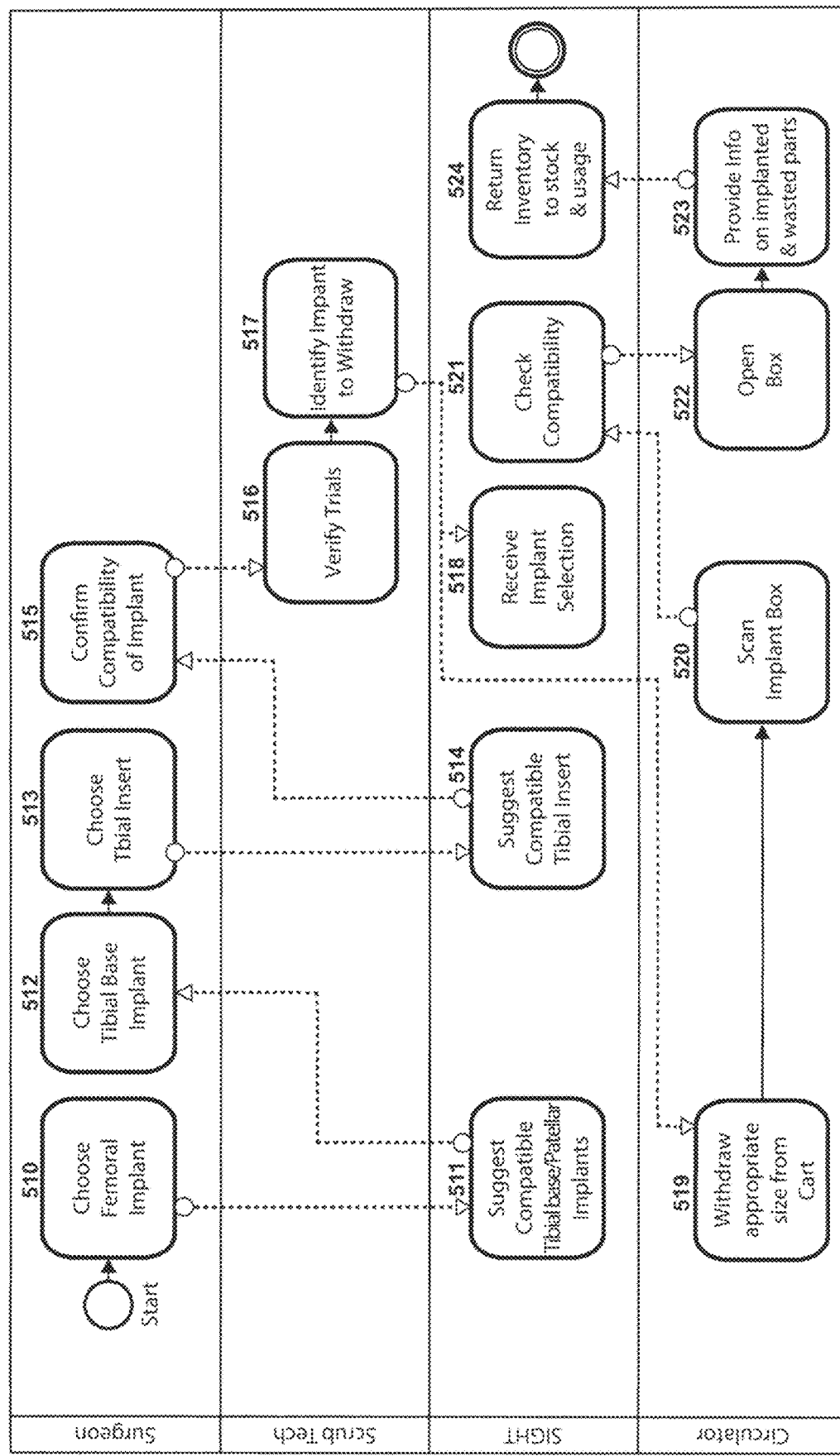

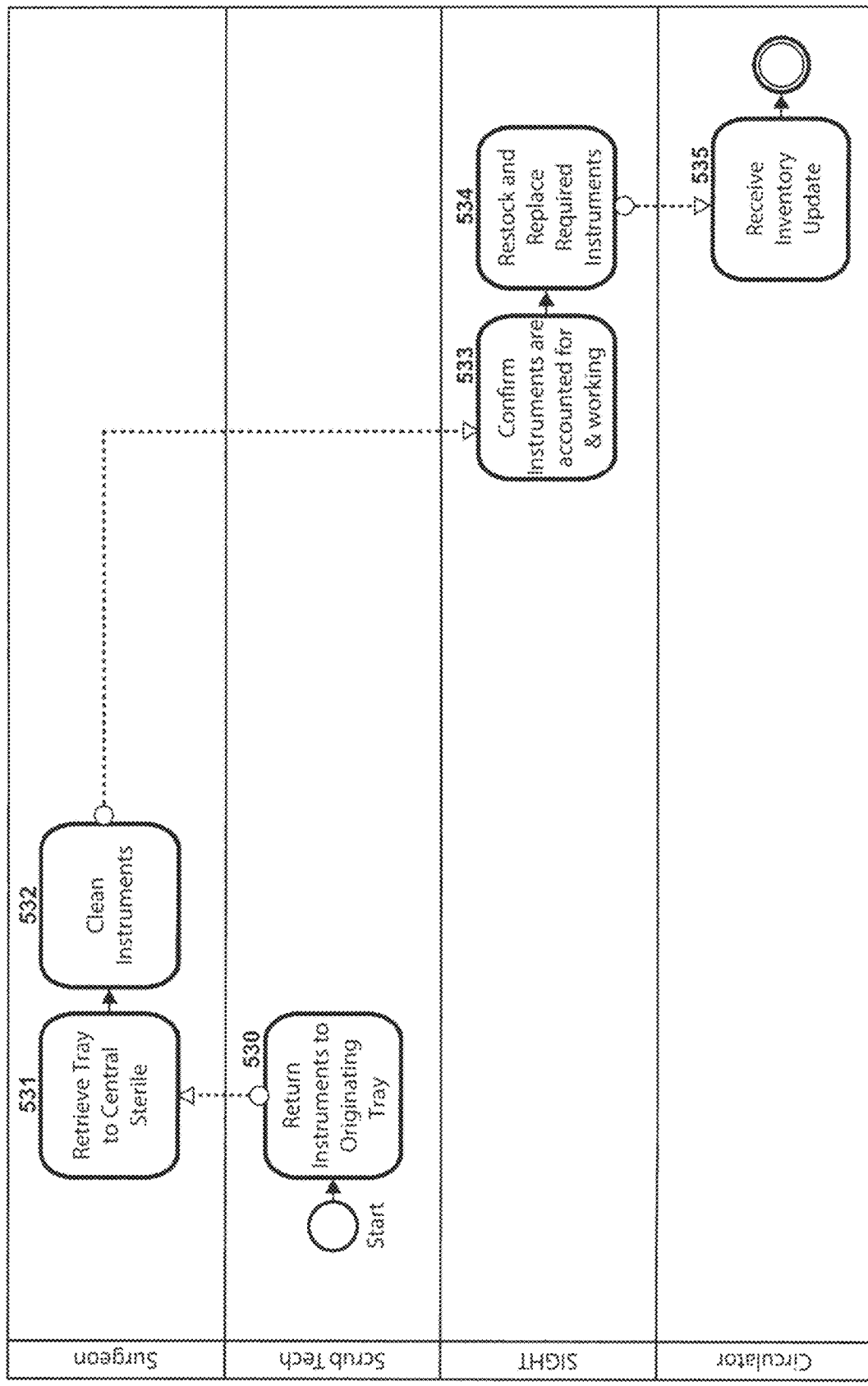

PROCESS AND APPARATUS FOR MANAGING MEDICAL DEVICE SELECTION AND IMPLANTATION

I. CROSS-REFERENCE TO RELATED APPLICATION

This application claims the benefit under 35 U.S.C. § 119(e) to U.S. Provisional Application Ser. No. 62/098,877 filed on Dec. 31, 2014, which is incorporated by reference herein in its entirety.

II. BACKGROUND OF INVENTION

The implantation of artificial joints typically involves a highly complex procedure of sizing, aligning, cutting, etc. in order to properly implant the artificial joint (hereinafter "implant"). To carry out this procedure, most implant manufactures provide a complex set of components and instruments over a range of sizes, from which the surgeon will likely need to select in order to accommodate the individual patient. The sheer number of components and instruments involved in the implant procedure has led to surgeons often preferring to have representatives of the implant manufacture assist in selecting and preparing the components and instruments for surgery. A system which standardizes, streamlines and organizes the number and types of components and instruments which must be transported into the operating theater would be a significant improvement in the art. Such a system would also reduce the possibility of the incorrect instrument (e.g., an incorrect cutting guide, sizing trial, etc.) being utilized during surgery. Additionally, it would be a significant improvement to provide a system which assists surgeons and other healthcare personnel to more efficiently use patient data in selecting implant sizes and types, tracking and maintaining an efficient inventory of implant components/instruments, and assisting surgery personnel in the efficient deployment of implant components/instruments during surgical procedures.

III. SUMMARY OF SELECTED EMBODIMENTS OF INVENTION

One embodiment of the invention is a method of selecting an instrument set for an orthopedic implant procedure to be performed on a patient by a physician. The method utilizes a computer programmed with a data structure configured to store (i) a set of implant components and implant instruments; and (ii) a set of surgical instruments utilized in performing the procedure. The method selects a sub-set of implant components and implant instruments based upon a determination of component types and then selects a sub-set of surgical instruments based upon a determination of surgical techniques. The method arranges the sub-set of surgical instruments and implant instruments into a substantially specific order based upon a determination of a sequence of bone cuts to be performed in the procedure.

Another embodiment of the invention is a method of managing implants. The method provides (i) an implant storage space, (ii) a storage sensor located proximate the storage space, the storage sensor configured to detect implant components, and (iii) a system computer communicating with the storage sensor. The method determines a set of implant components scheduled to depart the storage space, removes from the storage space the set of implant components scheduled to depart the storage space, and operates the storage sensor to communicate to the computer system that the set of implant components have been removed from the storage space.

A further embodiment of the invention is an implant management system which includes an implant storage space and a storage sensor located proximate the storage space, where the storage sensor is configured to detect implant components. The management system also includes a deployment sensor configured to detect implant components and a system computer communicating with the storage sensor and the deployment sensor. The system computer will have software configured to carry out the steps of: (i) receiving data representing a set of implant components scheduled to depart the implant storage space; (ii) receiving data indicating that the storage sensor has detected the set of implant components; and (iii) receiving data indicating that the deployment sensor has detected the set of implant components at a scheduled destination.

A further embodiment of the invention is a method of predicting a required size of an implant component utilizing a computer system. The method establishes on a user interface of the computer system a medical image of an anatomical part on a computer selectable coordinate system. The method allows a user to select multiple points on the coordinate system corresponding to specific anatomical features on the medical image, and then determines an anatomical distance between at least two of the multiple points selected by the user. Then the method compares the anatomical distance to a database which cross-references specific anatomical distances with a corresponding size of implant component.

Another embodiment of the invention is a method of selecting an instrument set for an orthopedic implant procedure to be performed on a patient by a physician. The method provides a computer system which is programmed with a data structure configured to store: i. a set of implant components and implant instruments; and ii. a set of surgical instruments utilized in performing the procedure. The method receives from a user interface computer an implant component size estimated for the patient and generates a sub-set of implant components and implant instruments based at least in part upon the implant component size estimated for the patient. The method generates a visual list of the sub-set of implant instruments in a specific order; and physically arranges the implant instruments substantially in the specific order in preparation for the implant procedure.

The foregoing is a summary of only a few embodiments and the invention includes many other embodiments, some described in the below detailed description and other not specifically described herein.

IV. BRIEF DESCRIPTION OF THE DRAWINGS

FIG. 4 illustrates selected anatomical features of a human leg bone utilized in certain embodiments of the present invention.

FIG. 5 is a flow chart illustrating one embodiment of a process for sizing a femoral implant component.

FIGS. 7A to 7C illustrate selected features on an medial-lateral view of the distal end of a femur.

FIG. 8 is a flow chart illustrating one embodiment of a process for sizing a tibial implant component.

FIG. 15A is a panel providing information on implant and surgical details.

FIG. 15B is a panel providing information on surgical cuts and instrument organization.

FIG. 15C is one embodiment of a summary chart which could be displayed on an operating room monitor.

FIG. 15D is one embodiment of a detailed instrument list with instrument images which could be displayed on an operating room monitor.

FIGS. 16A to 16J are panels illustrating instrument ordering in one embodiment of the invention.

FIG. 16K is an example of a label which could be fixed to an instrument tray.

FIG. 19A is a block diagram of electronic components associated with the cabinet of FIG. 18.

FIG. 19B is a block diagram of electronic components associated with a cart used in conjunction with the cabinet embodiment of FIG. 18.

FIGS. 20A to 20C are flow charts illustrating the functionality of computer enabled cabinet of FIG. 18.

FIG. 26 is a flow chart illustrating one method embodiment for transferring implant inventory to a deployment cart.

FIG. 27 is a flow chart illustrating one method embodiment for verifying and preparing implant instruments.

FIG. 28 is a flow chart illustrating one method embodiment for deploying implant components and instruments during surgery.

FIG. 29 is a flow chart illustrating one method embodiment for post-operative processing of implant and surgical instruments.

V. DETAILED DESCRIPTION OF SELECTED EMBODIMENTS

Figure 1:
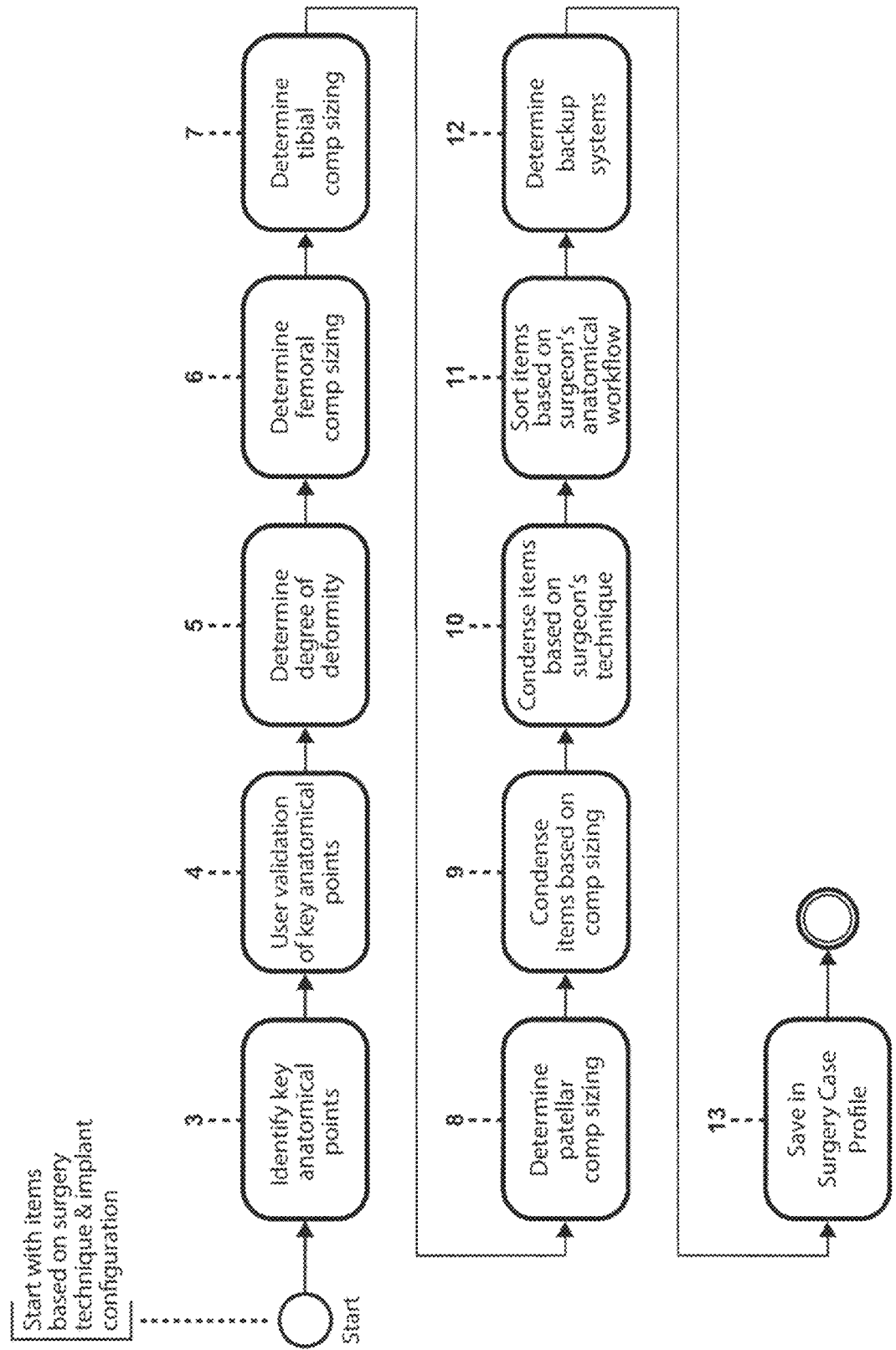
FIG. 1 is a flow chart illustrating one embodiment of an overall process for determining a reduced set of implant components and instruments.

One embodiment of the present invention includes a method of selecting an instrument set for an orthopedic implant procedure to be performed on a patient by a physician. In many embodiments, the implant device is for a joint such as the knee, hip, elbow, or shoulder, but could be for other bone joints or for implants unrelated to bones, such as pacemakers, stents, or soft tissue repairs of the shoulder and knee (e.g., implant components and instrumentation used in rotator cuff repair and/or ACL repair). "Implant procedure" as used herein means any medical procedure to implant, adjust, correct, or supplement an implant component in a human (or other animal) body. The methods and apparatuses described herein are intended to apply to existing and future developed implants and procedures. Many of the figures describe the method in terms of a total knee implant or total knee arthroplasty, but as suggested above, the method could apply equally to implants for other areas of the body. Certain of the described embodiments function to order a subset of "surgical instruments" and "implant instruments" which are associated with "implant components," all of which are defined below. Other embodiments function to assist in implant component inventory control and to assist operating room (OR) personnel in the deployment and implantation of the components.

As used herein, an "implant component" means a thing (e.g., a piece of tissue, prosthetic device, or other object) implanted in a human (or other animal) body as part of a surgical procedure and intended to remain in the body, temporarily or permanently, after the surgical procedure. As one nonlimiting example, implant components for a total knee arthroplasty could include a femoral component, a tibial component, and a patellar component. These components are provided in a range of sizes and configurations. For example, the femoral implant component may be "cruciate retaining" or "posterior stabilized," the tibial baseplate may be "modular" or "non-modular," and the patella component may be "onset" or "inset." A modular tibial component is formed of a tibial baseplate and a separate insert, while a non-modular tibial component is a single, unitary piece. Many implant components vary based upon bearing design, materials, and bone-implant fixation method, e.g., whether the implant components are affixed with cement or not cemented. A more complete listing of various implant components for one particular implant system is seen in Tables A1.1 to A1.23 in Appendix A, which appears in the related U.S. provisional application Ser. No. 62/098,877, filed on Dec. 31, 2014, which is incorporated by reference herein in its entirety. All reference herein to tables designated with the letter "A" (e.g., A1.1, A1.2, A2.1, etc.) refer to the Appendix in U.S. Ser. No. 62/098,877.

An "implant instrument" means a device generally in strict accordance with the type of implant being inserted and is typically supplied by an implant manufacture as an accessory to the implant components. Implant instruments are generally utilized to shape or facilitate the appropriate anatomy to fit the implant components. The femoral component, tibial component (baseplate and insert), and patellar component will have associated implant instruments. As one nonlimiting example, implant instruments for a total knee arthroplasty could include femoral trials, tibial baseplate trials, tibial insert trials, patella component trials, starters, gauges, bone files, bone alignment guides, femoral component sizers, CR Femoral component trials, CR femoral condyle drills, CR femoral component drivers, PS femoral component trials, PS notch cutting jigs, PS reamers, femoral trial component drivers, tibial insert trials, tibial insert component impactors, tibial drill guides, tibial punches, tibial insert trials, patellar drill guides, patellar trials. In general, implant instruments may include any instrument for component sizing, bone shaping, component preparation, or implanting (e.g., tools for alignment in the sagittal, coronal, and axial planes. A more complete listing of implant instruments for a conventional Total Knee System is seen in Tables A2.1 to A2.18.

A "surgical instrument" means a device the surgeon employs to organize and effect the surgical outcome, particularly in relation to implant procedures, but which is typically not considered an implant instrument. Surgical instruments include but are not necessarily limited to bone cutting and alignment instruments. As one nonlimiting example, bone cutting instruments for a total knee arthroplasty could include cutting guides, alignment guides, resection cutting guides and generally instruments for joint extremity alignment, balancing, measuring, and configuring. A more complete listing of surgical instruments suitable for use with a conventional implant system is seen in Tables A3.1 to A3.15.

Many of the figures of the present application illustrate methods and systems in terms of flow charts. It will be understood that the methods may be implemented by software running on a general purpose computer including a CPU, a user interface, and requisite memory components. A general purpose computer may include hand-held computers such as smart phones, particularly when a user is interfacing with other devices in the overall system.

Figure 17:
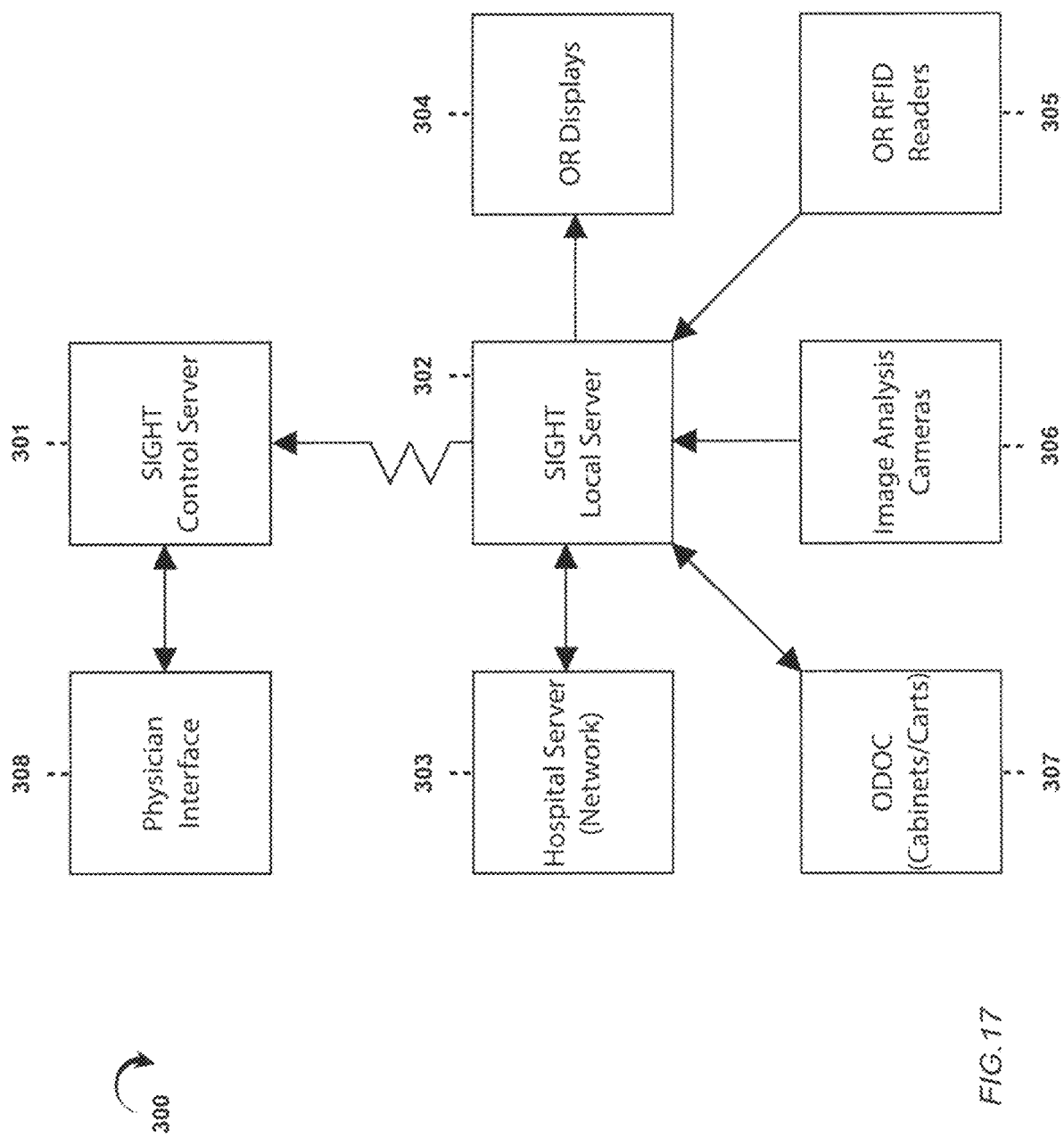
FIG. 17 is a system bock diagram showing components of an overall implant selection and deployment system.

FIG. 17 is a block diagram suggesting various components of one embodiment of the overall system 300 for carrying out the various methods described in this application. The general system 300 may sometimes be referred to herein by the trademark SIGHT™, e.g., the SIGHT system. In this embodiment, there is a central server 301 which will typically be remotely located from the other elements of the system. Most of the other elements seen in FIG. 17 are located at a hospital or other medical facility where the implant surgery is to be conducted. Thus, FIG. 17 shows a hospital network 303 and a "local" SIGHT server 302 located in the hospital and in communication with the central SIGHT server 301, for example through the hospital network 303. Although FIG. 17 only shows one set of elements which would generally be located at a particular hospital, it will be understood that the SIGHT central server 301 would be communicating with many different hospital networks 303 nationwide or even worldwide, with each hospital having a SIGHT local server 302. Where this application describes a "computer" or "computer system," these terms may include, as examples, central server 301, local server 302, or the two servers acting together as a single computer system.

Other system elements typically located in each hospital include one or more computer enabled cabinets 307 for holding and assisting in the management of the implant components and instruments. In this disclosure, the cabinets may be referred to by the trademark ODOC™, e.g., "ODOC cabinets" which are explained in greater detail below. In many embodiments, the SIGHT local server 302 is housed within the ODOC cabinet 307. Several other elements will communicate (typically through a wireless link such has the hospital's Wi-Fi system forming part of the hospital network 303) with the SIGHT local server 302. These other elements could include one or more computer displays 304 located in operating rooms, bar code scanners or RFID tag readers 305 located in places such as the ODOC cabinet and the hospital's operating room (OR). Alternatively or in addition to the bar code scanners or RFID readers, image analysis camera(s) 306 may form part of the overall system. Where the term "server" is used in the application, it is intended to mean in the broadest sense any general purpose or special purpose computer which can perform the functions described herein.

Normally each physician participating in the SIGHT system will have a physician interface 308 allowing physicians to send and receive information for carrying out the methods and object described herein. As one example, the physician interface could be the physician's smart phone or tablet running an app establishing communication with the SIGHT central server 301 and possibly with the local server 302 though the hospital network 303.

Figure 2:
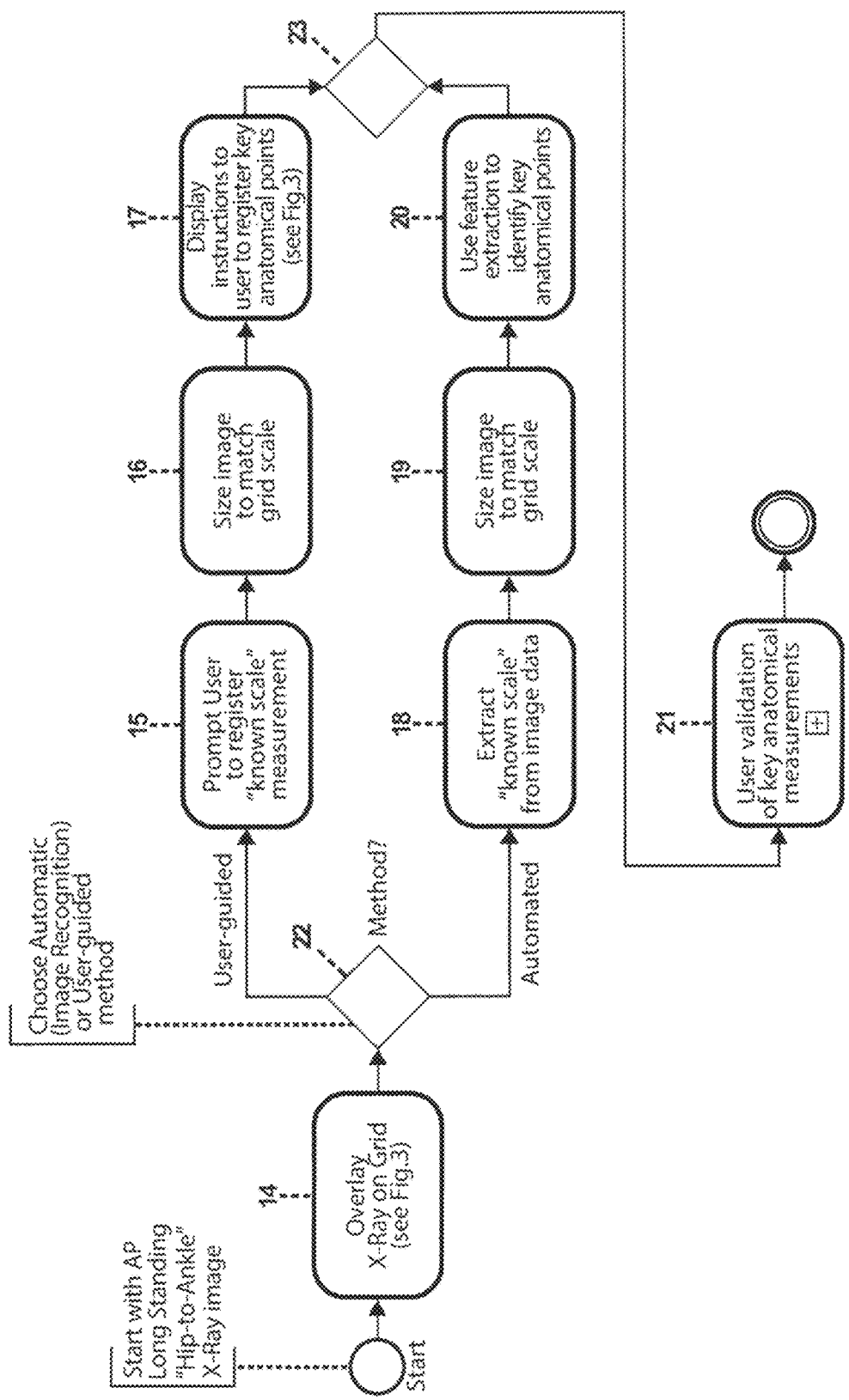
FIG. 2 is a flow chart illustrating one embodiment of a process for identifying key anatomical points of a bone joint.
Figure 3:
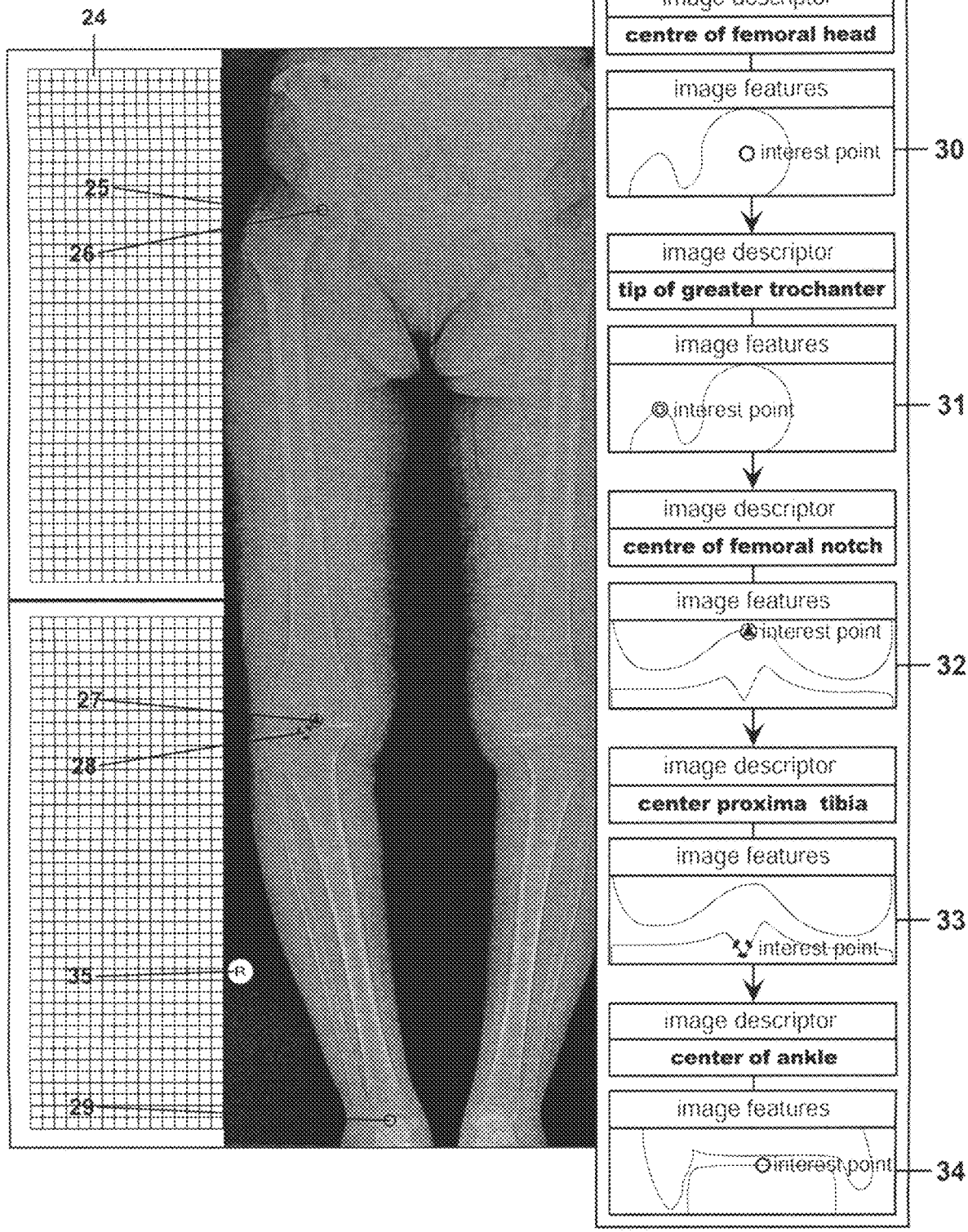
FIG. 3 illustrates one embodiment of a system for identifying key anatomical points on a medical image.

Examples of the functionality of the SIGHT system suggested by FIG. 17 can be seen starting with FIG. 1. FIG. 1 is a comparatively high-level flow chart illustrating a series of steps taken in one example process for obtaining implant sizing information and selecting a narrowed set of implant components and implant instruments most likely to be utilized in the implant procedure being contemplated. Step 3 in FIG. 1 suggests how the process begins with identifying key anatomical points related to the bone joint or other body part being replaced or corrected with the implant. This step is shown in more detail in the flow chart of FIG. 2. In step 14, a medical image on a radiological monitor or other type of monitor is overlayed or superimposed on a computer selectable coordinate system, which may be a system forming a grid based upon individual pixels or groups of pixels allowing a user to select "points" on the image (image coordinates) with a mouse controlled cursor or touch screen technology. As used herein, "medical image" means any conventional or future developed technique for imaging body parts, including x-rays, MRIs, CT scans, and ultrasound. FIG. 3 illustrates conceptually an x-ray of human legs overlayed on the computer grid 24. At step 22 of FIG. 2, the user is prompted as to whether to utilize a user guided procedure for identifying selecting key anatomical features or to allow the software to perform an image recognition-based algorithm in order to identify the anatomical features. In the user guided procedure, step 15 of FIG. 2 prompts the user to register the scale of the medical image. For example, FIG. 3 shows the scaling marker 35 which allows the computer grid scale to be correlated with the medical image scale. In step 16, the user employs the scaling marker to size the medical image to the computer grid scale as is well known in conventional image viewing software. As suggested in step 17 and FIG. 3, the method includes displaying on the monitor adjacent to the medical image a representation of the anatomical points of interest. For example, FIG. 3 shows images illustrating the location of the center of the femoral head (image 30), the tip of the greater trochanter (image 31), the center of the femoral notch (image 32), the center of the proximal tibia (image 33), and the center of the ankle (image 34). Using these images as guides, the user may "click" on the corresponding anatomical point on the medical image as suggested by the markers showing the center of the femoral head 26, the tip of the greater trochanter 25, the center of the femoral notch 27, the center of the proximal tibia 28, and the center of the ankle 29. As an alternative procedure, FIG. 2's steps 18-20 could employ a feature recognition algorithm which automatically identifies these series of points, e.g., algorithms such as those found in The Mathworks Inc.'s computer vision system toolbox. Regardless of which procedure is utilized to identify the anatomical features or points of interest, a final step (21) in the method will have the user (e.g., the surgeon ultimately responsible for the implant procedure) validate the correctness of anatomical points selected and any measurements resulting therefrom. Although the above example describes an image with a scaling marker, there are medical image formats which do not necessarily require any scaling, e.g., images conforming to the Digital Imagining and Communications in Medicine (DICOM) format.

One anatomical characteristic which may be derived from the identified anatomical points is the degree of varus or valgus deformity suffered by the knee which is the subject of the medical image (step 5 in FIG. 1). FIG. 4 illustrates one method the system could use for determining the degree of varus or valgus deformity. A first line or the "femoral mechanical axis" ("FMA") is defined as the line between the center of the femoral head (CFH) and the center of the femoral notch (CFN). A second line or the "tibial mechanical axis" ("TMA") is defined as the line between the center of the proximal tibia (CPT) and the center of the ankle (CA). Because the FMA and TMA are created on the electronically rendered grid system, the relative angle between the FMA and TMA may readily be determined by the computer system.

This angle between the FMA and TMA is ultimately utilized to determine the degree of valgus or varus deformity. As a matter of convention, whether a knee has a valgus or varus deformity is determined by the relative position of the knee joint center ("JC") relative to the weight bearing axis ("WBA") of the leg. The WBA is defined as the line running between the CFH and the CA. A neutrally aligned leg (no measurable varus or valgus deformity) will have the FMA and TMA running colinearly through the WBA. Where the JC is lateral to the WBA, the deformity is considered varus. Where the JC is medial to the WBA, the deformity is considered valgus. In the FIG. 4 embodiment, the degree of deformity is calculated by first determining the hip-knee-ankle ("HKA") angle, which may be defined as the lateral angle formed by the FMA and TMA. Thereafter, the absolute value the HKA angle minus 180° is defined as the degree of deformity. FIG. 4 suggests the WBA having been aligned with the vertical axis of the grid system, but this is not strictly necessary since the computer system may calculate the HKA angle regardless of the relative orientation of the WBA and other lines involved.

Figures 6A, 6B, 6C:
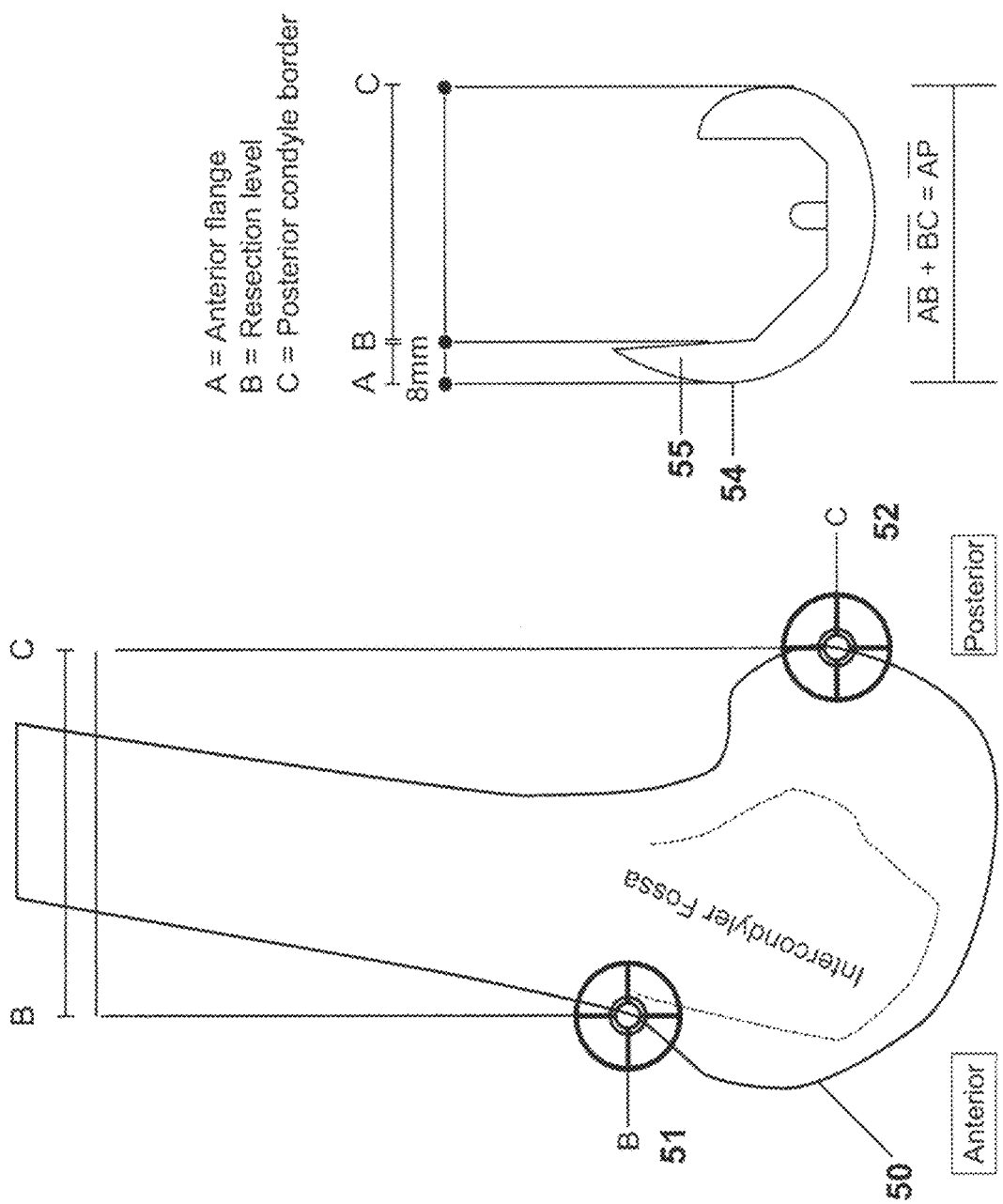
FIGS. 6A to 6C illustrate selected features on an anterior-posterior view of the distal end of a femur.

Returning to FIG. 1, step 6, the next basic implant parameter to be determined is the femoral component size. Different example methods for determining this parameter are illustrated in FIGS. 5 to 7. FIG. 5, step 42 begins with prompting the user to select one of two methods for determining a distance related to the femoral component size. Both methods are based upon registering key points of interest for the femur, for example by using the electronic grid system described in reference to FIG. 3. In the method of step 43, an anterior-posterior ("AP") distance is used to determine femur size. FIG. 6A illustrates an AP view of the distal femur end 50 where the user will register two points in step 45, the anterior femoral resection level 51 and the posterior condyle border 52. Thereafter, in step 47 of FIG. 5, the system calculates the femoral component size. In this calculation, the distance between points 51 and 52 (shown in FIG. 6A as the distance BC along the anterior-posterior line) is added to the thickness of the anterior flange 55 (FIG. 6B) of the femoral implant component 54. This distance AC in FIG. 6B is then utilized to find the closest "AP distance" shown in the femoral AP sizing chart of FIG. 6C. For example, if the distance AC were 59 mm, then the using the sizing chart in FIG. 6C, the system would estimate a size 3 femoral component.

An alternative method is disclosed in step 44 of FIG. 5. In this step, the points suggested in FIG. 7A are utilized. These points are the medial posterior condyle border 58 and the lateral posterior condyle border 59, which are typically recognizable in a medial/lateral medical image of the distal femur end (as suggested by dashed lines in FIG. 7A). In step 45 of FIG. 5, the user registers the medial posterior condyle border 58 and the lateral posterior condyle border 59. The system measures this distance (illustrated as distance DE in FIG. 7B) which is referred to as the medial-lateral or "ML" distance of the distal femoral end. In step 47 of FIG. 5, the system utilizes the determined distance DE to find the closest "ML distance" shown in the femoral ML sizing chart of FIG. 7C. For example, if the distance ML were 65 mm, then the using the sizing chart in FIG. 7C, the system would estimate a size 3 femoral component.

Figure 9B:
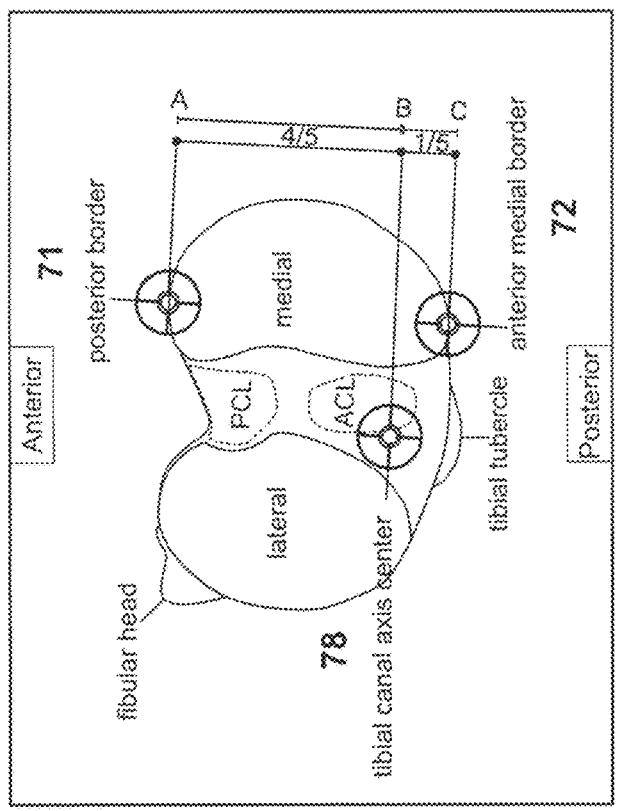
FIGS. 9A and 9B illustrate selected features on an anterior-posterior view of the proximal end of a tibia.
Figure 10:
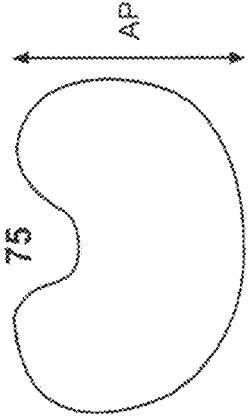
FIG. 10 illustrate a tibial component sizing chart.
Figure 9A:
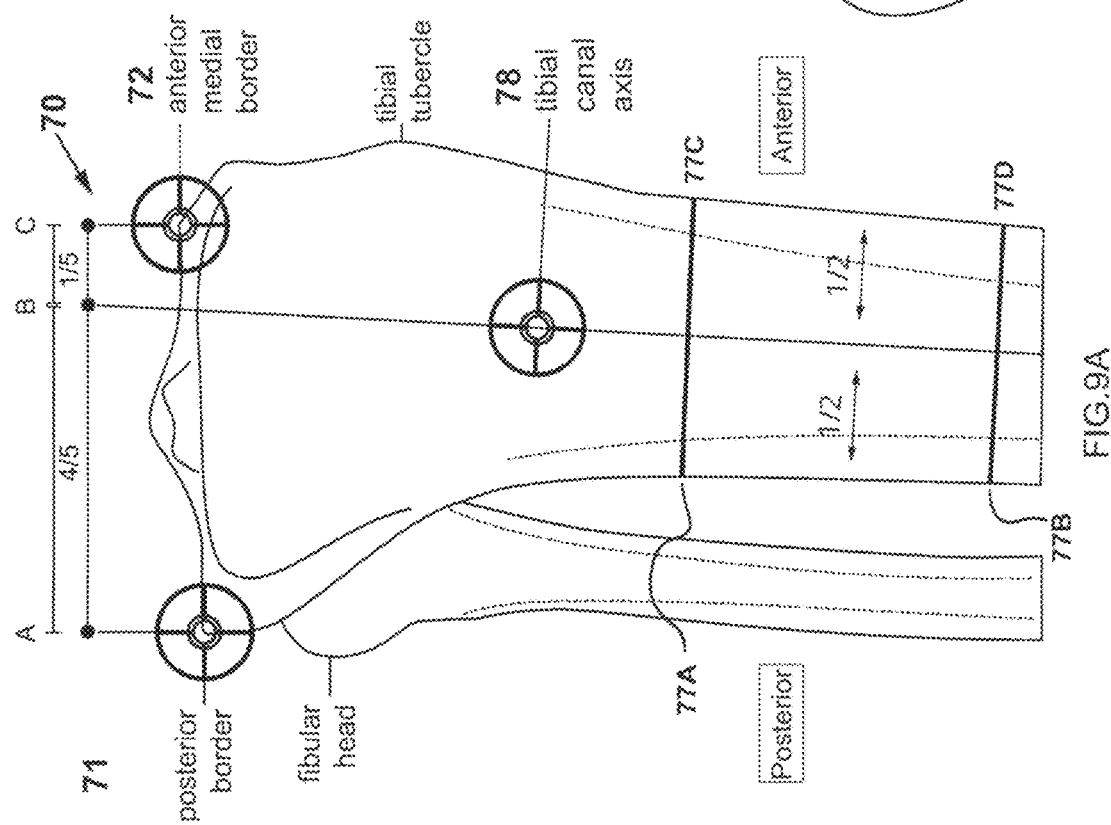

Once the femoral component size is calculated or estimated, FIG. 1, step 7 determines the tibial component size. This selection process is shown in more detail in FIGS. 8 to 11. FIG. 8 suggests how the user may select in step 60 one (or both) of two alternative techniques for estimating the tibial base plate size. The first alternative is determining direct AP measurement of the tibial plateau which is best understood with reference to FIG. 9A. FIG. 9A suggests the user selecting (step 62a of FIG. 8) the posterior border 71 of the tibial plateau and the anterior medial border 72 of the tibial plateau. The system then determines the distance between these points in step 63a. The measured "AP" distance between points 71 and 72 is then correlated with the "AP" distance on the tibial base plate as suggested in step 64 of FIG. 8 and FIG. 10. The base plate size is estimated by finding the closest standard AP distance (for the different base plate sizes as shown in the chart of FIG. 10) corresponding to the measured AP distance between points 71 and 72. As a nonlimiting example, if the measured AP distance between points 71 and 72 were 46 mm, then base plate size 3 having the standard AP distance of 47 mm would be the estimated base plate size. FIG. 9B illustrates how the AP distance on the tibial plateau may be measured from an axial view of the tibial plateau, e.g., an axial view generated from a MRI or similar technique. Again, the user is able to select anatomical points corresponding with the posterior border 71 and the anterior medial border 72 of the tibial plateau.

FIG. 9A also suggests an alternative method for measuring the AP distance by utilizing the "tibial canal axis" 78. The tibial canal axis is a line running lengthwise along the center of the tibia. The tibial canal axis will be located by a user selecting four points 77A to 77D along the tibial medial borders as shown in FIG. 9A. The tibial canal axis 78 is calculated as the line running through the midpoints between line 77A-77C and line 77B-77D. The tibial canal axis is extended to intersect (at point B) the line AC between the posterior medial border 71 and the anterior medial border 72 of the tibial plateau. The AP distance for the sizing chart may then be calculated as five times the distance BC or $5/4^{th}$ the distance AB.

Figure 11B:
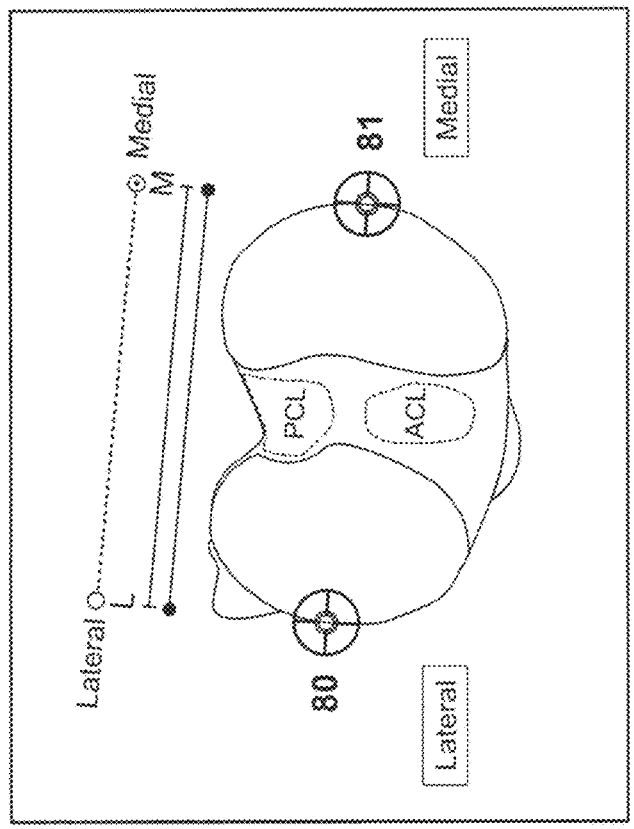
FIGS. 11A to 11C illustrate selected features on an medial-lateral view of the proximal end of a tibia.
Figure 11C:
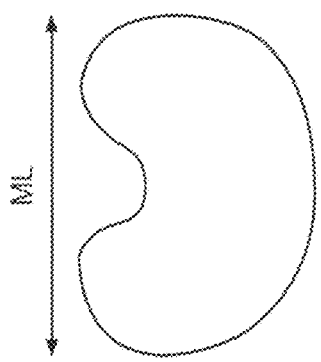
Figure 11A:
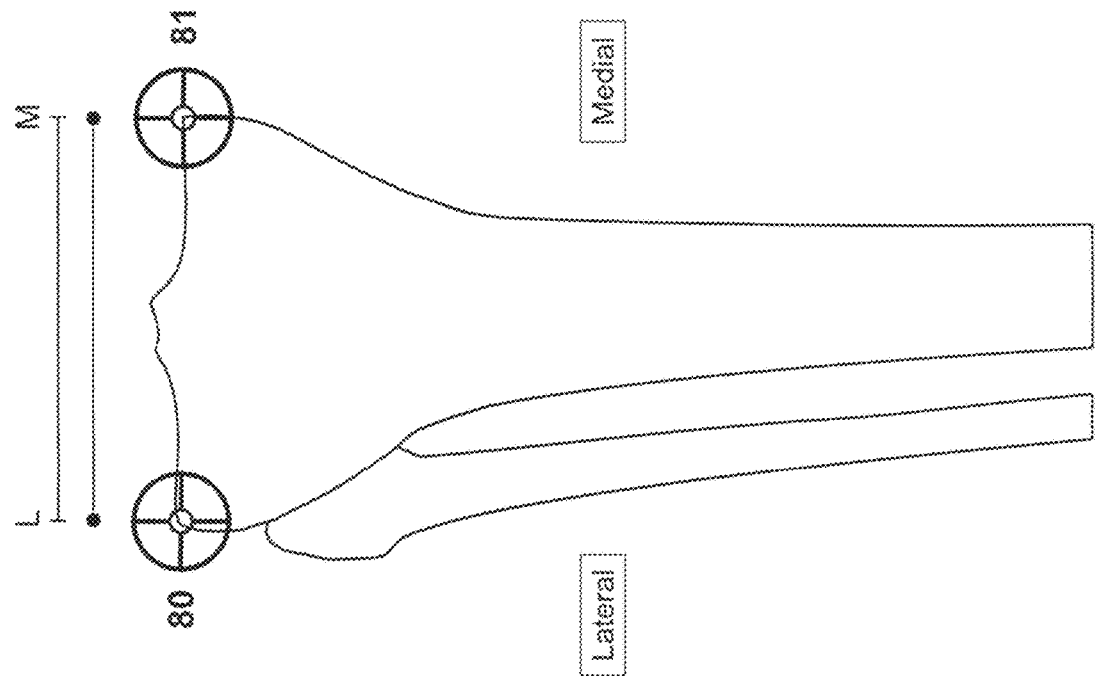

An alternative measurement technique is seen in steps 62b and 63b of FIG. 8 where a medial to lateral measurement is made across the tibial plateau. FIG. 11A illustrates how the user will select (step 62b in FIG. 8) the lateral most point 80 on the tibial plateau and the medial most point 81 on the tibial plateau, allowing the system to compute a measured ML distance from the medical image in step 63b. This can again be compared to the closest standard ML distance on the various sizes of tibial base plates as suggested in FIG. 11C, thereby rendering an estimated base plate size as per step 64. FIG. 11C illustrates how the same points may be selected on an axial view of the tibial plateau in order to obtain the measured ML distance.

Once the estimated tibial base plate size is determined in step 64 of FIG. 8, the user is prompted to verify the estimated size in step 65. In other words, the user, e.g., the surgeon performing the implant procedure, is expected to use his or her professional judgment to confirm that the implant size estimated by the algorithm is consistent will of the particular patient details known to the surgeon and the surgeon's overall experience with implant procedures.

A determination of patellar component size (if necessary) is made in step 8 of FIG. 1. The surgeon may measure the width and/or thickness of the patient's patellar or the surgeon may estimate a patellar component based upon his or her judgement considering the size of the femoral and tibial components. In some implant procedures, the patient's existing patellar may be utilized with the implanted femoral and tibial components.

Figure 12A:
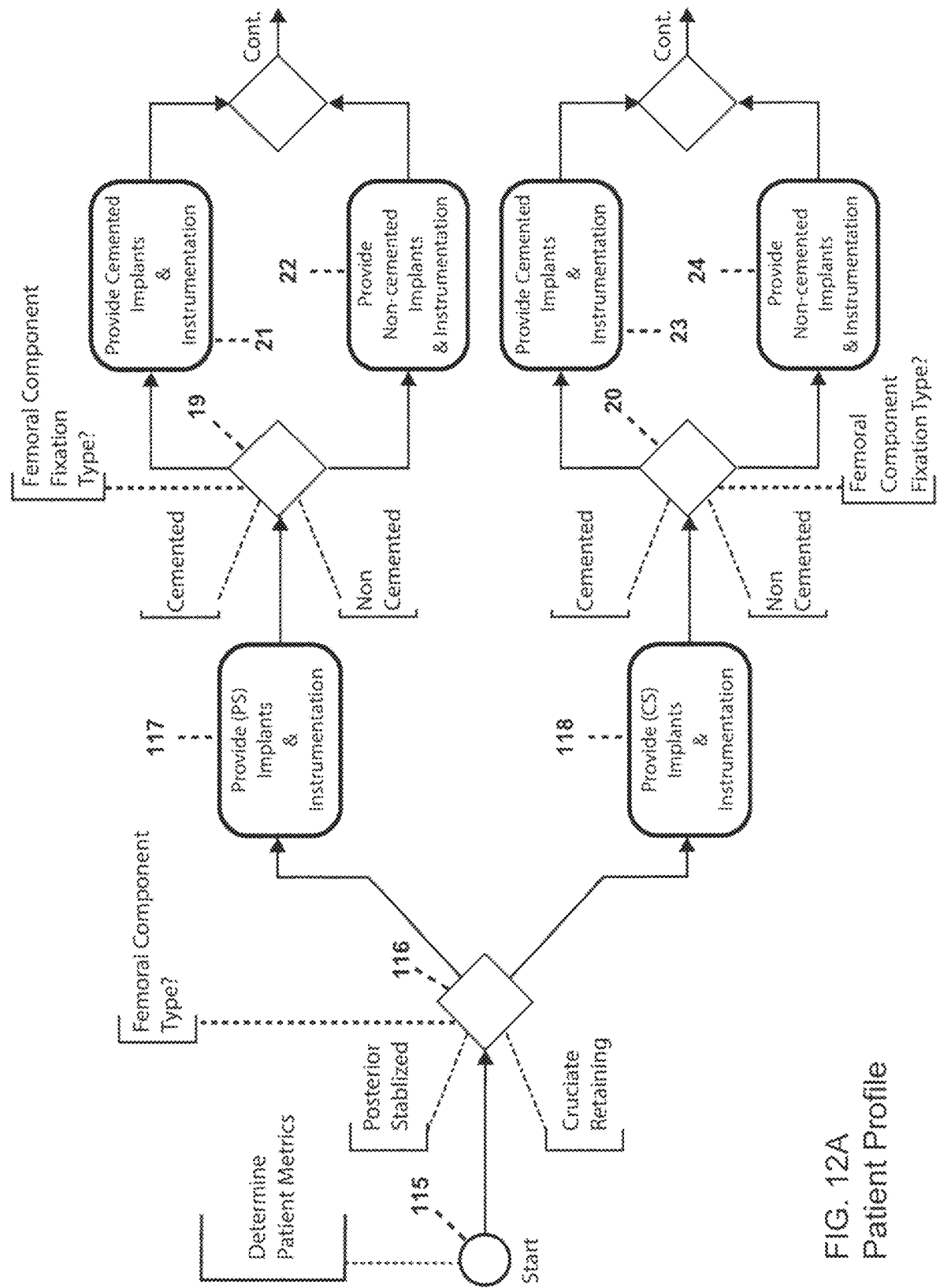
FIGS. 12A to 12C are a flow chart illustrating one embodiment for selecting implant components and related instruments utilized in a total knee arthroplasty.
Figure 12B:
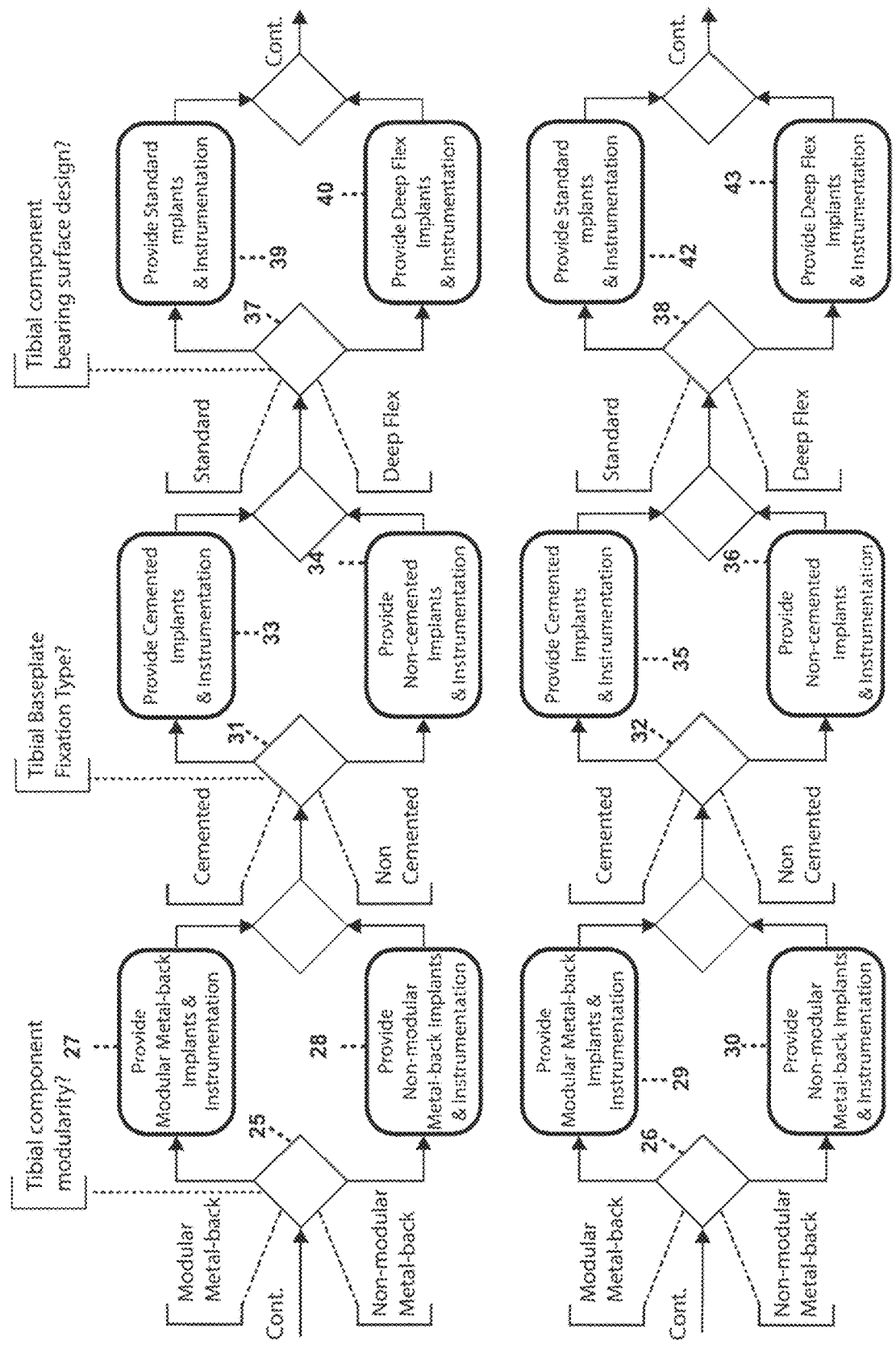
Figure 12C:
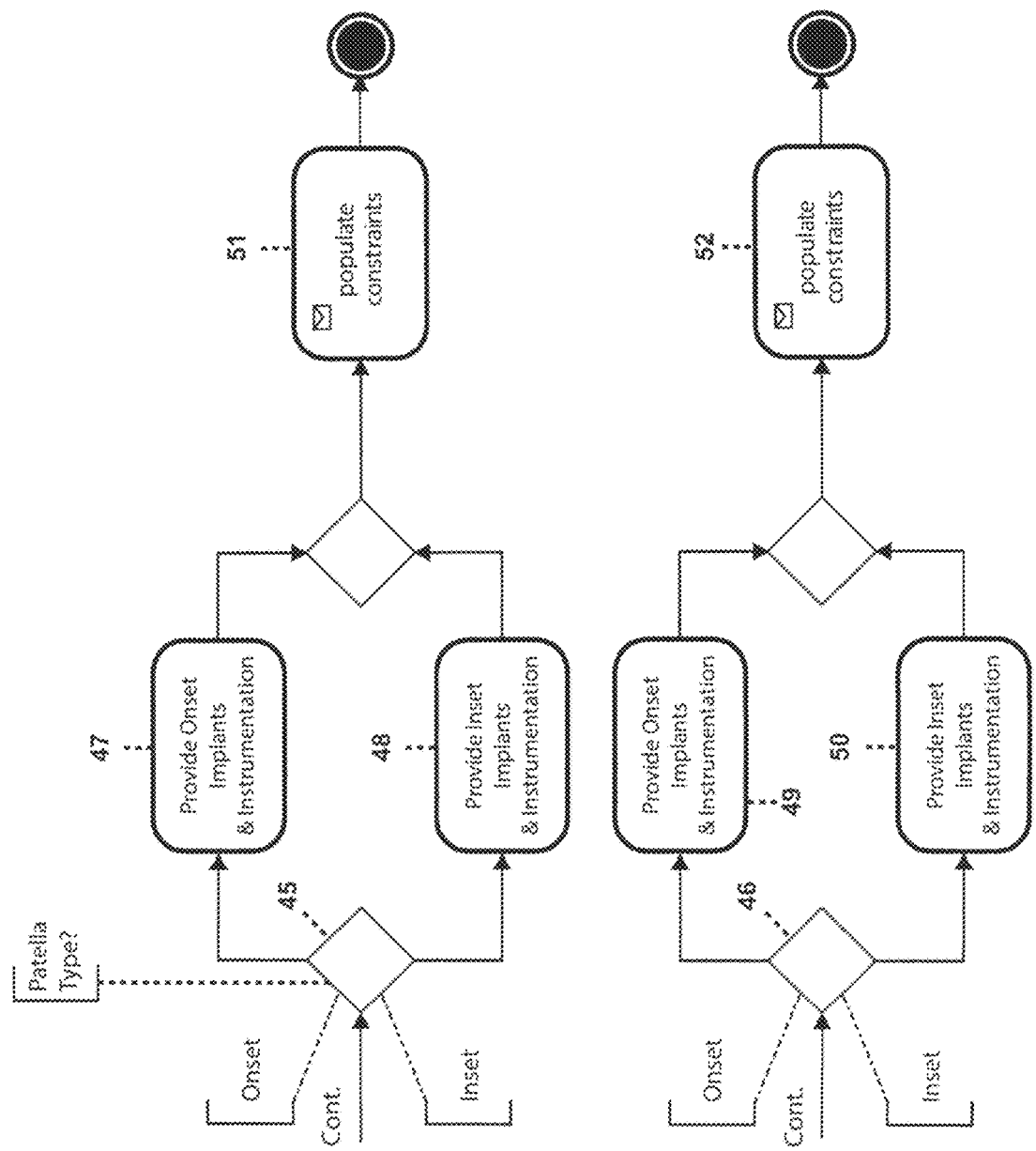

Once femoral component size, tibial component size, and patellar component size have been estimated, FIG. 1, step 9 involves the condensing, i.e., reduction in the number of components, of the implant components and implant instruments. FIGS. 12A to 12C illustrate one method for selecting certain implant components and implant instruments based upon certain information such as "patient metrics" and "implant component types." In one embodiment, "patient metrics" means patient anatomical information relating to an implant procedure. As one nonlimiting example, patient metrics for a total knee arthroplasty could include patient age, sex, extremity (e.g., left knee/right knee), initial deformity, activity level, insert constraint, and component size range. As suggested in the above FIGS. 5 and 8, the system may determine an estimated femoral component size and tibial component size, e.g., size 4 for the femoral component and size 3 for the tibial component. The "component size range" would typically be the next size above and below the estimated component size, e.g., 3, 4, and 5 for the femoral component and 2, 3, and 4, for the tibial component. It is a common practice to prepare for surgery not only the single most likely component size, but also a size above and below. This practice addresses the possibility that upon accessing the joint and cutting/shaping the femur or tibia, the surgeon will determine that the component size above or below the initially estimated is the better size selection.

Further patient metrics could include patient clinical presentations, initial limb deformity analysis, boney architecture, (e.g., bone valgus/varus degree measurement as described above, overall bone health and/or need for additional implant component augments), and potential complicating factors (e.g., previous surgeries). For purposes of describing one embodiment in reference to FIGS. 12 to 16, the following patient metrics will be assumed: Age: 62; Sex: Male; Extremity: Right Knee Joint; Initial Deformity: 12° Valgus; Activity Level: Moderately Active; Insert Constraint: PS Standard; Femoral Component Size Range: 3, 4, 5; Tibial Component Size Range: 2, 3, 4; Patellar Component Size Range: 32 mm, 35 mm, 38 mm. "Implant component type" means a variation of implant type/style. As one nonlimiting example, component types for a total knee arthroplasty could be (i) post stabilized vs. cruciate retaining in regards to femoral components, (ii) modular metal-back vs. monblock metal-back for tibial components, (iii) standard, deep flex, or constrained for tibial insert components, and (iv) onset vs. inset for patellar components. Both femoral and tibial components may have cemented and uncemented variations.

In the initial step 115 seen in FIG. 12A, the patient metrics for the patient receiving the implant are determined. In this embodiment, "determining" or "determination" means reaching a decision or obtaining a needed value or other information. For example, a program receiving user input of a requested value (e.g., through a drop down menu) is considered a "determination" of that value. Likewise, values pre-existing in a database and directly accessed by a software program can also be a "determination." Examples of determinations made in the disclosed embodiments include providing an implant component type (e.g., posterior stabilized or cruciate retaining femoral components), an implant instrument type (e.g., standard, deep flex or constrained tibial insert type), or a surgical instrument type (e.g., milling device, resection guide and power saw only for the patella resurfacing technique). Naturally, this list is merely illustrative and many other "determinations" of relevant information would be made in obvious variations of the currently described embodiments. For the purposes of the FIG. 12A embodiment, it is assumed a that a determination has been made to use a fixed bearing, non-constrained implant type.

In many embodiments, it is contemplated that patient metrics would be initially uploaded to the SIGHT system by the patient's surgeon or other treating physician via a physician interface such as suggested in FIG. 17.

In FIG. 12A, after receiving or "determining" the patient metrics in step 115, step 116 determines whether the femoral component type will be "post stabilized" or "cruciate retaining" (e.g., a decision, like others regarding implant type, made by the surgeon in consultation with the patient prior to implantation). This decision results in the selection of implant components and implant instruments (step 117 or 118) associated with the selected femoral component type. For example, assuming posterior stabilized ("PS") is selected, then the range of femoral implant components is narrowed to those seen in tables A1.3 and A1.4 and those cruciate retaining ("CR") implant components seen in tables A1.1 and A1.2 may be eliminated from consideration. Likewise, certain implant instruments such as the CR Femoral Trials in tables A2.3 and A2.4 may be eliminated from consideration. Additionally, the patient metrics provided size information and left/right selection, allows a further narrowing of potential implant components. In step 119, a determination is made as to whether the femoral component will be cemented or uncemented (with a similar determination made in step 118 if cruciate retaining was chosen). FIG. 15A lists the selections determined in the steps seen in FIGS. 12A to 12C.

Continuing with the earlier example, if a cemented PS femoral component is selected, step 121 will return a subset of femoral components from table A1.3. Assuming patient metrics providing a right side implant and a #4 size, a list of PS cemented femoral implant components as shown in Table 1 below will be identified. As suggested above, in many embodiments, if a single best estimate size is provided from patient metrics, the next implant component (and implant instrument) size above and below the anticipated size is provided in order to allow these other sizes to be used as alternatives to the initially estimated size. Thus, the identification of size #4 in patient metrics will result in the return of sizes #3, #4, and #5 for all implant components and implant instruments (where size is applicable). Alternatively, a size range may be provided in the original patient metrics (e.g., see above assumed patient metrics). At step 121, a determination of a reduced set of implants and instruments from tables A1.3, A2.1, and A2.5 may be made according to the below tables 1 and 2:

TABLE 1

PS - Femoral Implant Comp (Cemented).

Femoral Component PS, Cemented, #3 right
Femoral Component PS, Cemented, #4 right
Femoral Component PS, Cemented, #5 right

TABLE 2

PS - Femoral Implant Instruments (Cemented).

Femoral Component PS, trial Cemented, #3 right
Femoral Component PS, trial Cemented, #4 right
Femoral Component PS, trial Cemented, #5 right
Cemented femoral impactor
PS cutting jig drill guide
PS reamer
PS Notch cutting jig, #3
PS Notch cutting jig, #4
PS Notch cutting jig, #5
PS housing punch
PS housing impactor In FIG. 12B, the selection process continues for the tibial component of the implant. Because the assumption in the above example was posterior stabilized, this example will look at step 125 to determine whether the tibial/insert component type is modular metal-back or non-modular metal-back. However, it can be seen in FIG. 12B that a parallel selection process takes place beginning at step 126 if cruciate retaining had been selected in regards to femoral type. It will be assumed for purposes of this example, that in step 125 modular metal-back is selected, reducing the responsive components to Tables A1.5, A1.6, and A1.9 to A1.11. Step 131 again narrows this selection down in terms of cemented and uncemented and if cemented is selected, further reduces responsive components to Tables A1.6 and Tables A1.9 to A1.11. The implant instruments are now limited to Tables A2.8 and A2.11 to A2.13. A final determination is made in step 137 as to whether the tibial component bearing surface design is "standard" or "deep flex" as seen in Tables A1.9, A1.10, and A1.11, respectively. If "standard" type is determined, the implant components and implant instruments will be:

TABLE 3

PS - Tibial Baseplate Implant Comp (Cemented).

Cemented, Tibial baseplate #3
Cemented, Tibial baseplate #4
Cemented, Tibial baseplate #5

TABLE 4

PS - Tibial Insert Implant Comp (Cemented).

Tibial insert PS, Standard, #3 × 9 mm
Tibial insert PS, Standard, #3 × 11 mm
Tibial insert PS, Standard, #3 × 13 mm
Tibial insert PS, Standard, #3 × 15 mm
Tibial insert PS, Standard, #3 × 18 mm
Tibial insert PS, Standard, #4 × 9 mm
Tibial insert PS, Standard, #4 × 11 mm
Tibial insert PS, Standard, #4 × 13 mm
Tibial insert PS, Standard, #4 × 15 mm
Tibial insert PS, Standard, #4 × 18 mm
Tibial insert PS, Standard, #5 × 9 mm
Tibial insert PS, Standard, #5 × 11 mm
Tibial insert PS, Standard, #5 × 13 mm

TABLE 4-continued

PS - Tibial Insert Implant Comp (Cemented).

Tibial insert PS, Standard, #5 × 15 mm
Tibial insert PS, Standard, #5 × 18 mm

TABLE 5

PS - Tibial Baseplate Implant Instruments (Cemented).

Cemented, Tibial baseplate trial #3
Cemented, Tibial baseplate trial #4
Cemented, Tibial baseplate trail #5
Tibial baseplate driver
Tibial baseplate trial handle
Tibial drill
Tibial drill guide
Cemented tibial punch handle
Cemented tibial punch, S
Cemented tibial punch, M
Cemented tibial punch, L

TABLE 6

PS - Tibial Insert Implant Instruments (Standard).

Tibial insert trial PS, Standard, #3 × 9 mm
Tibial insert trial PS, Standard, #3 × 11 mm
Tibial insert trial PS, Standard, #3 × 13 mm
Tibial insert trial PS, Standard, #3 × 15 mm
Tibial insert trial PS, Standard, #3 × 18 mm
Tibial insert trial PS, Standard, #4 × 9 mm
Tibial insert trial PS, Standard, #4 × 11 mm
Tibial insert trial PS, Standard, #4 × 13 mm
Tibial insert trial PS, Standard, #4 × 15 mm
Tibial insert trial PS, Standard, #4 × 18 mm
Tibial insert trial PS, Standard, #5 × 9 mm
Tibial insert trial PS, Standard, #5 × 11 mm
Tibial insert trial PS, Standard, #5 × 13 mm
Tibial insert trial PS, Standard, #5 × 15 mm
Tibial insert trial PS, Standard, #5 × 18 mm
Universal Insert impactot
Insert extractor FIG. 12C illustrates the final steps in the implant component and implant instrument selection process. In step 145, it is determined whether the patellar component type is onset or inset. The implant component options are set out in tables A1.22 and A1.23, while the implant instrument options are seen in tables A2.14 and A2.16. If onset is determined in step 145, then the returned implant components and instruments in step 147 are:

TABLE 7

Onset Patellar Implant Components.

Patella, onset, 32 mm
Patella, onset, 35 mm
Patella, onset, 38 mm

TABLE 8

PS - Onset Patellar Implant Instruments.

trial, onset, 32 mm Patellar
trial, onset, 35 mm Patellar
trial, onset, 38 mm Patellar
On set patellar peg drill TABLE 8-continued PS - Onset Patellar Implant Instruments.

On set patellar drill guide, 32 mm
On set patellar drill guide, 35 mm
On set patellar drill guide, 38 mm In step 151 of FIG. 12C, all components and instruments in Tables 1 to 8 are returned.

Figure 13A:
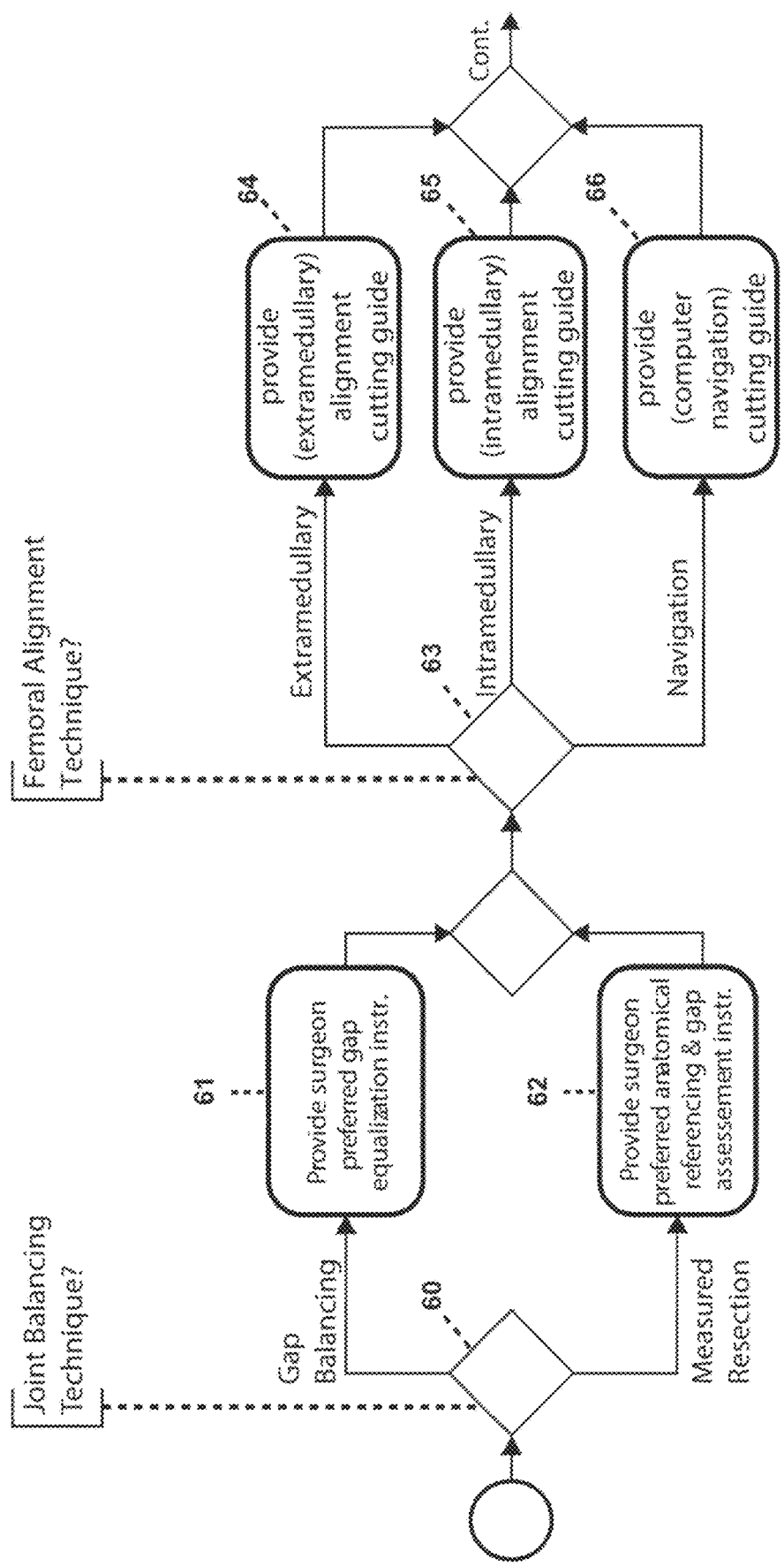
FIGS. 13A to 13B are a flow chart illustrating one embodiment for selecting surgical instruments utilized in a total knee arthroplasty.
Figure 13B:
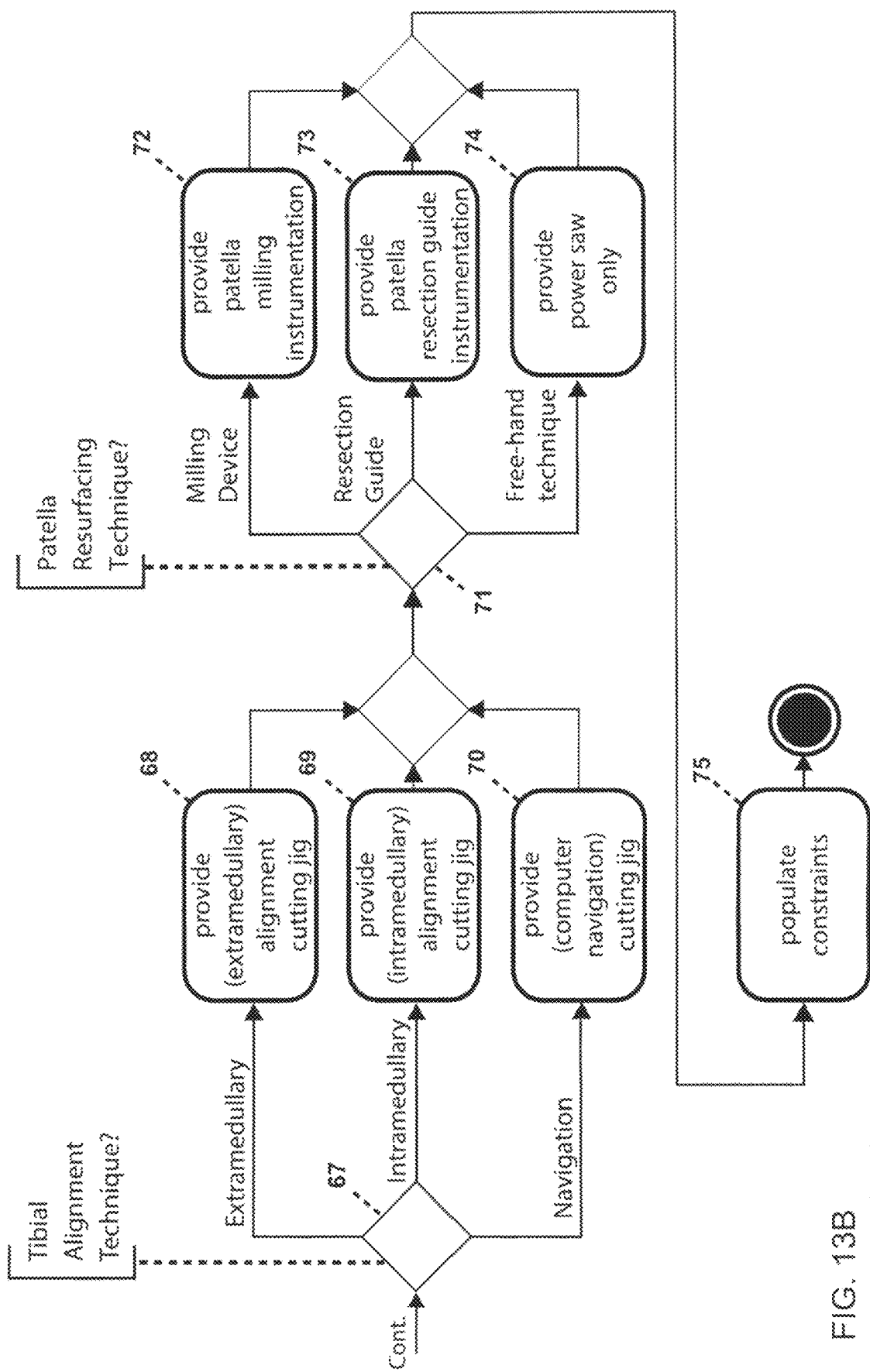

FIGS. 13A and 13B illustrate one process which may be utilized in selecting the surgical instruments utilized in the implant procedure. This process is based upon the "surgical technique" utilized by the surgeon. Examples of surgical techniques which may be utilized in a knee replacement procedure include joint balancing technique (gap balancing vs. measured resections), distal femoral cut valgus alignment technique (extramedullary, intramedullary, or navigation), tibia cut varus/valgus alignment technique (extramedullary, intramedullary, or navigation), and patella resurfacing technique (milling device, resection guide, or free-hand). An exemplary set of surgical instruments which might be used in conjunction with a conventional implant system are listed in Tables A3.1 to A3.15. In step 160 of FIG. 13A, it is determined what joint balancing technique is to be utilized. If the gap balancing technique is chosen, step 161 returns the surgeon's preferred gap equalization instruments (e.g., AP sizer, AP cutting guide, implant specific tensioners, etc.) and these will correspond to the surgical instruments in Table A3.1. If measured resection is chosen, step 162 returns the surgeon's preferred gap equalization instruments which will correspond to Table A3.2. Assuming measured resection is determined and taking into account the previous patient metrics, step 162 would return the instruments:

TABLE 9

Measured Resection Femoral Instruments.

Femoral sizing & rotation guide, sz 1-7
Ant/Post Ref, 4-n-1 cutting guide, #3
Ant/Post Ref, 4-n-1 cutting guide, #3
Ant/Post Ref, 4-n-1 cutting guide, #3
Anchoring pins
Pin driver In step 163, it will be determined whether the femoral alignment technique (distal femoral cut) will be extramedullary, intramedullary, or via computer assistance. The instruments related to these selections are illustrated in Tables A3.3, A3.4, and A3.5, respectively. If intramedullary is determined, step 165 would return the instruments:

TABLE 10

Valgus Alignment Instruments (distal femoral cut).

Femoral drill
Femoral IM rod
Femoral IM alignment guide
Femoral IM valgus guide, right
Distal femoral alignment guide
Distal femoral cutting guide
Anchoring Pins
Pin Driver As seen in FIG. 13B, a similar determination is made in step 167 regarding the tibial alignment technique related to the proximal tibial cutting. The cutting may be extramedullary, intramedullary, or via computer assistance, with the instruments related to these selections being illustrated in Tables A3.6, A3.7, and A3.8, respectively. If extramedullary is determined, step 168 would return the instruments:

TABLE 11

Varus/Valgus Alignment Instruments (proximal tibial cut).

Tibial stylus
Tibial cutting guide, right
Tibial EM alignment guide
Tibial alignment rod
Anchoring Pins
Pin Driver Next in FIG. 13B, a determination is made in step 171 regarding the patella resurfacing technique. The resurfacing technique may be via a milling device, resection guide, or a free-hand technique, with the instruments related to these selections being illustrated in Tables A3.10, A3.11, and A3.12, respectively. If resection guide is determined, step 173 would return the instruments:
Table 12. Patella Resurfacing Instruments (Patella Cut).
Patellar resection guide
Patellar caliper In step 175 of FIG. 13B, the populating constraints step results in the instruments in Tables 9 to 12 being returned.

Once the subset of implant components, implant instruments, and surgical instruments are selected through the above described process, a further series of steps in the illustrated embodiment accomplishes the ordering the implant instruments and the surgical instruments. One series of steps for ordering the instruments based on the surgeon's preferred sequence of making bone cuts is suggested in FIG. 14. This procedure anticipates different surgeons will make the bone cuts in different orders. However, for purposes of illustrating one example of utilizing this process, it will be assumed that the sequence of cutting is: (1) distal femoral; (2) proximal tibial; (3) anterior femoral; (4) posterior femoral; (5) anterior femoral chamfer; (6) posterior femoral chamfer; and (7) patellar.

Figure 14:
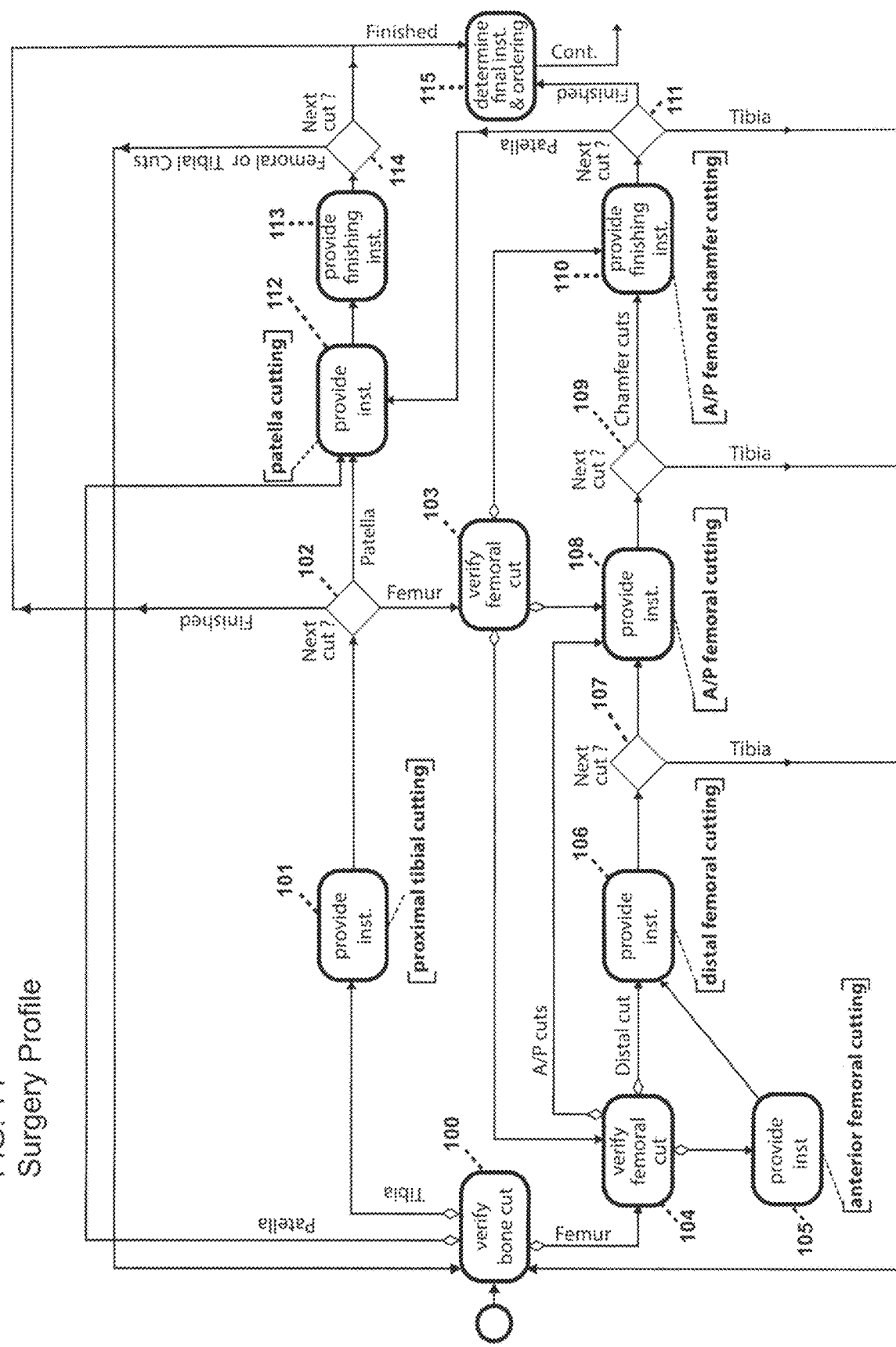
FIG. 14 is a flow chart illustrating one embodiment of bone cutting sequences utilized in a total knee arthroplasty.

At step 200 in FIG. 14, it is determined which bone and particular cut the surgeon prefers to make first in the procedure. If the femur is selected (step 204), a further selection of either an anterior femoral cut or a distal femoral cut must be determined, which will return a respective set of instruments in steps 205 or 206. Since distal femoral is being assumed for this example, the instruments would correspond to Table 10 above (which are also seen in FIG. 16A). After this cut, a decision is made at step 207 regarding whether the next cut will be the proximal tibial cut or the anterior/posterior (A/P) femoral cut. Assuming proximal tibial, the logic flow is to step 201 (through step 200) which returns the instrument set of Table 11 (FIG. 16B). In step 202, a decision is made whether all cuts have been made (cutting finished), to proceed to the patella cut, or to proceed to the remaining femoral cuts. Assuming the next cut to be the remaining femoral cuts, step 208 will return the instruments seen in Table 9 (FIG. 16D). Since the tibial cuts have been made, step 209 directs the logic flow to A/P femoral chamfer cutting, which in step 210 returns some of the implant instruments from Table 2 together with the cutting guides from Table 9 (FIG. 16F). At step 211, the logic flow moves to the patellar cut in step 212, which returns the instruments from Tables 8 and 12 related to the patellar cut (FIG. 16G). In step 213, the previously cut flat section of bone is sized for the appropriate patella implant, with holes being drilled using the correct sizing instrument. If no further cuts are to be made in step 214, then in step 215, the final instrument set is returned and ordered as further described with reference to FIG. 15B.

FIG. 15B suggests the order of not only surgical instruments from the logic of FIG. 14, but also associated implant instruments. For example, after the proximal tibla cutting step, the surgeon will typically make an extension gap check. This involves the series of surgical instruments (see FIG. 16C) such as the extension gap spacer block, the spacer block alignment rod, and a series of gap gauges (see Table A3.14). Thus, these implant and/or surgical instruments will be incorporated into the ordered set of instruments. Similarly, after the A/P femoral cut, a flexion gap check is carried out using similar surgical instruments as suggested in FIG. 16E (see Table A3.13). After the patellar cutting and finishing step, a series of trials are made using all the trial components, i.e., the femoral component, the tibial baseplate, the tibial insert, and patellar trials (see FIG. 16H). Certain other surgical instruments (e.g., femoral trial component driver, tibial insert trial impactor and extractor—see Table A3.15) will be associated with these trials. Another set of instruments (see FIG. 16I) will be associated with any tibial finishing. Finally, the instruments seen in FIG. 16J will be provided for the actual implant component fixation to the prepared femur and tibia.

It should be observed from FIGS. 16A to 16J that certain instruments are used multiple times in the sequence of preparing bone cuts and carrying out the trials. For example, the gap gauges shown in FIG. 16C for the extension gap check are also used in the extension gap check as suggested by FIG. 16E. Likewise, A/P cutting guides seen in FIG. 16D are also part of the instruments seen in FIG. 16F. Typically, a second set of these repeatedly used instruments is not provided, but rather the same instruments are used at these different stages of the procedure. Of course, this does not rule out certain embodiments providing redundant sets of instruments.

In certain embodiments, these instruments suggested in FIGS. 16A to 16J will simply be provided as an ordered list, e.g., printed out or displayed on a monitor (as described in more detail below). In many other embodiments, the instruments will be placed in some type of containers (e.g., a "surgical trays") in the specific order illustrated in FIGS. 16A to 16J, in which the instruments are sterilized prior to being brought into the operating theater. A conventional surgical tray often has several "sub-trays" or "layers" which stack one on top of the other within the main surgical tray. These layers may even include divider spaces which further subdivide the layers into "sections." Thus, each of FIGS. 16A to 16J are not intended to each represent the contents of a separate surgical tray. Rather, the sub-sets of instruments in FIGS. 16A to 16J could each be place on separate layers or even separate sections. The instruments may be arranged in a manner that is most convenient and efficient given the shape, size, and number of instruments while generally following the order seen in FIGS. 16A to 16J. It is not necessary that the instruments be place in the exact order determined by the selection method, i.e., the instruments do not need to be in the exact order seen in FIGS. 16A to 16J. For example, in FIG. 16A, the femoral drill need not necessarily be placed directly next to the femoral IM rod or the anchoring pins directly next to the pin driver. It is sufficient that the order of the instruments is "substantially specific" to that determined by the method. Substantially specific means that there is at least a 60% correlation between the instrument order determined by the method and the instruments as ordered in the surgical trays (or other containers). In alternative embodiments, this correlation could be at least 65%, 70%, 75%, 80%, 85%, 90%, or 95%. This less than exact correlation could also apply if the final result is merely a list of instruments as opposed to physical trays.

In many embodiments, the trays(s) with the assembled components/instruments will have one or more labels placed on the trays. FIG. 16K illustrates one example of a label 250 which could be applied to the trays. This example label has blocks 251 for written text such as system name (e.g., the manufacturer's trademark for the product), version (e.g. "standard"), set # (e.g., which unit of multiple units are available at the location), tray name (e.g., "femoral alignment" tray), format or type of system (e.g., "minimally invasive"), manufacture reference number, etc. These labels will also have one or more bar codes which associate certain information in the SIGHT system to this label. For example, the "ODOC Assignment" bar code 252 provides information on which ODOC cabinet the tray components originate from or are assigned to. The Table of Contents bar code 253 will be associated with a list of instruments in the tray. The OR Setup Diagram bar code 254 will be associated with a diagram illustrating how the instruments should be set up in the OR, e.g., see FIGS. 15C and 15D showing an example of setup diagrams. Thus, one example the above described method could include the steps of assembling the implant instruments in a tray and placing a bar code on the tray, where the bar code associates the tray with a particular instrument order stored in the computer system.

It will be understood that in many embodiments, the instruments themselves will have unique bar codes attached directly to the instruments. This allows the instruments to be scanned and identified by the SIGHT system at different steps of the various procedures described herein. It will also be understood that where bar codes are mentioned, other tracking technologies could be substituted, e.g., RFID tags rather than bar codes and RFID readers rather than bar code scanners.

FIGS. 15C and 15D illustrate one example of how the reduced instrument set may be used to assist an orthopedic implant procedure in an operating room with a display communicating with a computer system (e.g., OR display 304 and SIGHT local server 302 in FIG. 17). The computer system may loaded with a sub-set of surgical instruments and implant instruments arranged into a substantially specific order based upon a determination of a sequence of bone cuts to be performed in the procedure. The surgical instruments and implant instruments may be displayed in the substantially specific order in different formats. For example, FIG. 15C provides an overview of the entire procedure listing sequentially information such as the process step number, the instrument group, the cut number, the table of contents reference, and activity type. Additionally, FIG. 15D suggests how steps may be broken down with images of the instruments presented in the order of their use. This visual display of the instruments would help less highly skilled OR assistants organize the instruments prior to surgery and would also assist the surgeon during surgery to keep track of each successive instrument and step to be carried out. Although only two steps are shown in FIG. 15D for the sake of brevity, it will be understood that each step in FIG. 15C would be presented in sequence and with instrument images on the OR display as suggested by FIG. 15D.

In one embodiment, the above method would include the steps of first loading on the computer system a sub-set of surgical instruments and implant instruments arranged into a substantially specific order based upon a determination of a sequence of bone cuts to be performed in the procedure. Next would be presented on the display the surgical instruments and implant instruments in the substantially specific order. Then on the display, the user would advance through the substantially specific order of the surgical instruments and implant instruments as a user orders the instruments on an operating room table.

A related method embodiment would involve the computer system having a data structure storing (i) a set of implant components and implant instruments and (ii) a set of surgical instruments utilized in performing the procedure. The computer system would receive from a user interface computer an implant component size estimated for the patient, generate a sub-set of implant components and implant instruments based at least in part upon the implant component size estimated for the patient, and then generate a visual list of the sub-set of implant instruments in a specific order. Then the OR assistant would physically arrange the implant instruments substantially in the specific order in preparation for the implant procedure.

In addition to obtaining a reduced instrument set for the implant size most compatible with the particular patient (a "simple primary" non-constrained implant system), a severe varus or valgus deformity and other patient specific circumstances may render it is advisable to have a more constrained set of implant components/instruments (revision implants) in case the surgeon determines during surgery that a more specialized implant system is preferable. Thus, FIG. 1, step 12 prompts the user (surgeon) to determine a backup instrument set. In one embodiment, the determination of whether and which backup system is advisable may be made on factor such as set out in Table 13 appearing below.

For example, in the case of a "primary" knee replacement (i.e., the first time the patient is receiving a replacement of the knee in question), the procedure is likely to be considered a "simple primary" procedure if there is minimal valgus/varus deformity and there are no other complicating factors. In such a case, the surgeon may determine there is no need for a backup system. On the other hand, in the case of what the surgeon considers to be moderate valgus/varus deformity (e.g., <15 degrees) and/or moderate instability and bone loss, the surgeon may consider the case as a "complicated primary" and opt to have available a non-constrained implant system with augmentation. In other words, the implant system will have full rotational and medial/lateral freedom of movement, but the base portions of the implant components may require supporting metal augmentation to compensate for a greater degree of bone removal during preparation of the knee to receive the implant. In cases of greater degrees of deformity (e.g., >15 degrees) and complicating factors as significant existing knee instability and/or bone loss, the surgeon may consider the case as a complex primary and select a semi-constrained implant system with augmentation. This implant system provides medial/lateral constraint (e.g., to compensate for compromised knee ligaments), but still allows significant rotational freedom.

Another class of knee replacement procedures are "revisions" where the patient has already had at least one replacement of the knee at issue. For a "standard" revision procedure, i.e., no significant complicating factors beyond the replacement of a previous implant, the surgeon may wish to have a semi-constrained implant system as described immediately above. In revision cases where there is very severe bone loss and/or moderate deformity, the surgeon may consider the case to be a "complicated revision" and opt for fully constrained implant system with augmentation. This implant system allows the least freedom of movement and is functionally a hinged system. The same backup implant system would be selected in a "complex revision" where there is severe bone loss, instability, and a comparatively high degree of deformity (e.g., >15 degrees).

Figure 18:
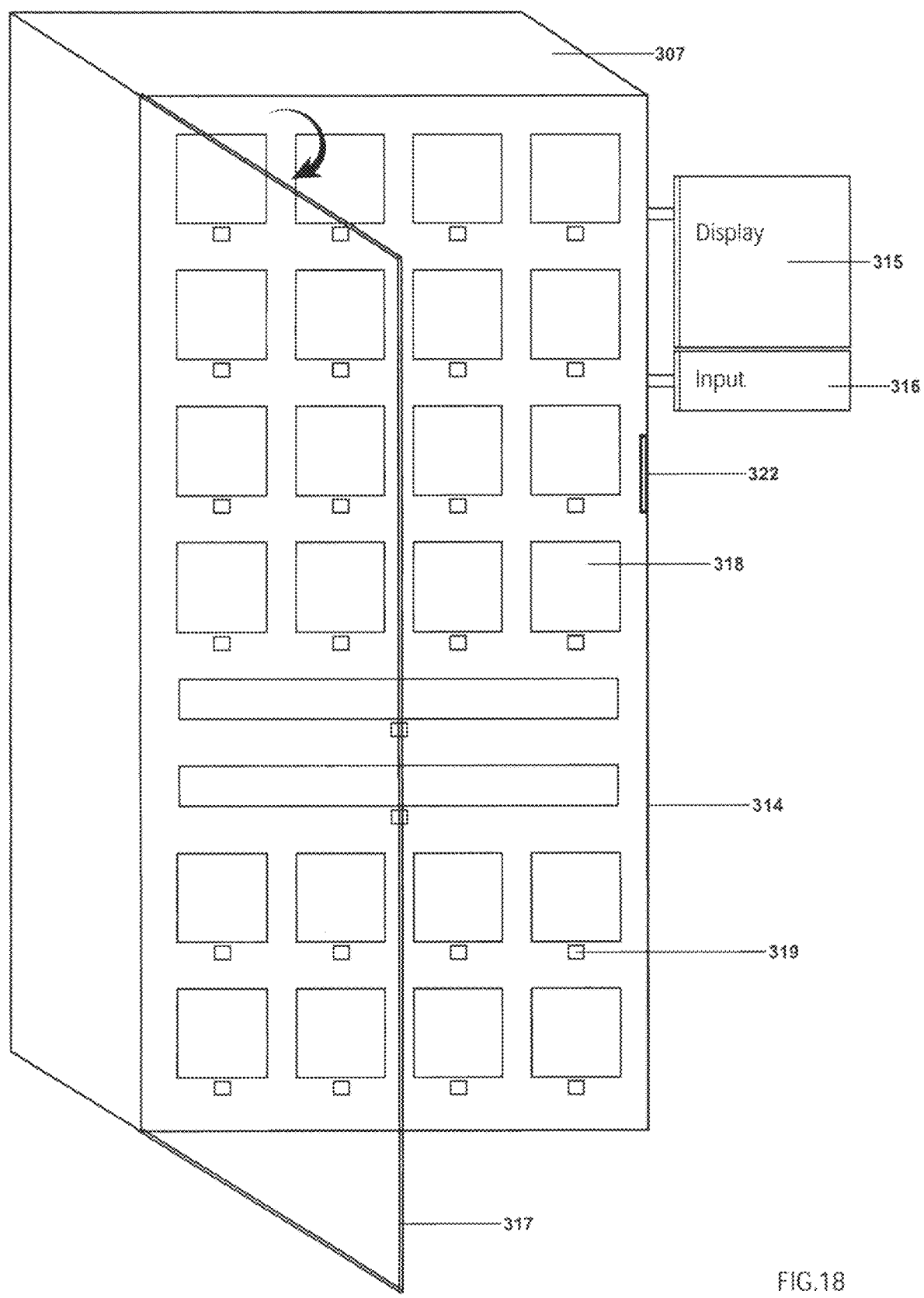
FIG. 18 illustrates one embodiment of a computer enabled cabinet for storing and tracking implant components and instruments.

As mentioned above in reference to FIG. 17, one of the components of the overall SIGHT system is the cabinets 307 or the "ODOC" cabinets. FIG. 18 illustrates one embodiment the cabinet 307 having a cabinet body 314 with various

TABLE 13

| Complexity/Backup Criteria | |
|---|---|
| 1. Simple Primary<br>Minimal Varus/Valgus & Rotational Constraining Prosthesis Configurations<br>Multiple CR & PS Component Options (i.e., Material, Bearing Surface, Fixation, Fit, Function)<br>Modular & Non-Modular Tibial Components | Implant System<br>Non Constrained |
| 2. Complicated Primary<br>Minimal Varus/Valgus & Rotational Constraining Prosthesis Configurations<br>Multiple CR & PS Component Options (i.e., Material, Bearing Surface, Fixation, Fit, Function)<br>Modular & Non-Modular Tibial Components<br>Augmentation Options for Managing Moderate Instability & Bone Loss | Implant System<br>Non Constrained<br>w/augmentation |
| 3. Complex Primary<br>Varus/Valgus & Rotational Constraining Prosthesis Configurations<br>Deep Femoral Box/Cam w/ Large Tibial Post<br>Modular Femoral & Tibial Components<br>Several Augmentation Options for Managing Moderate to Severe Instability & Bone Loss | Implant System<br>Semi Constrained<br>w/augmentation<br>(non-hinged) |
| 4. Standard Revision | |
| 5. Complicated Revision<br>Most Constrainting Prosthesis Configurations<br>Axle/Hinge Links Femoral & Tibial Components<br>Modular Femoral & Tibial Components<br>Modular Augmentation Options to Manage Global Instability & Massive Bone Loss | Implant System<br>Fully Constrained<br>w/augmentation<br>(hinged) |
| 6. Complex Revision/Limb Salvage | | bins or shelves 318 formed in the cabinet body. A door 317 with a computer controlled locking mechanism 322 will control access to cabinet 307. Many embodiments of the cabinet will have a user interface such as the display 315 and input 316. In some embodiments the input 316 is the touch screen and forms part of display 315. In other embodiments, the input 316 may be formed of a touchpad or a keyboard/mouse combination. One example of the electronic components which could control cabinet 307 is seen in FIG. 19A. Thus, there is a CPU or controller 320 which communicates with a memory 325, the display 315, and a network interface 324, which again could be a Wi-Fi link to the hospital network. The embodiment of FIG. 19 shows the controller 320 interfacing with a keyboard 316A, a mouse 316B, bar code scanner (or RFID reader) 321, door release (or door lock control) 322, and biometric reader 323. The bar code scanner (or RFID reader) 321 may be considered a type of "storage sensor" since it functions to sense or read components stored in cabinet 307. The biometric reader may be any conventional or future develop device for reading a biometric parameter, e.g., finger print, retina scan, voice recognition, etc. The biometric sensor will typically be used to authorize user access to cabinet 307, i.e., the biometric sensor allowing the controller 320 to identify the presence of an authorized user and activating the door release.

Although FIG. 18 illustrates a cabinet with a lockable door, other embodiments could employ any type of implant storage space, whether enclosed or not. The use of an RFID reader which detects the entry into or exit from the storage space of a RFID tagged object would reduce the importance of a lockable enclosure. As alluded to above, the ODOC cabinet controller 320 may in many embodiments act as the local SIGHT server 302 referenced in FIG. 17.

In many embodiments of the SIGHT system, the ODOC cabinet 307 will operate in conjunction with a computer enabled cart 330. The cart will allow system users to place trays of implant components from the ODOC cabinet onto the cart for wheeling into the operating room. FIG. 19B shows the electronic components associated with one embodiment of the cart. Thus cart 330 may include a contoller/CPU 334 operating in conjunction with memory 331, bar code scanner (or RFID tag reader) 333, network interface (e.g., Wi-Fi link) 335, and a user interface including display 332, mouse 336, and keyboard 337. The bar code scanner 333 may be considered a type of "deployment sensor" since it is used to sense or read bar codes during the deployment of the implant components and instruments, i.e., when the cart is in the OR or other location distant from the storage cabinet. Additional aspects of cart 330's functionality are explained in conjunction with the flow charts of FIGS. 20A to 20C and other figures described herein.

FIG. 20A illustrates a basic operational sequence when a user accesses an ODOC cabinet 307. The log-in step 340 involves the entry of an access code or reading of the appropriate biometric parameter by a biometric sensor. The user will select through the user interface in step 341 the intended action, for example removal (i.e., the "take function") of an item from the cabinet. In step 342, the user selects the patient (allowing the system to associate a set of implants and instruments with a patient's name) and in step 343 the cabinet controller activates the door release. As the user removes each item, the item is scanned in step 344. Thereafter, the cabinet door release re-locks and the controller terminates the functional sequence. In alternative embodiments utilizing an RFID reader rather than a bar code scanner, the cabinet controller could take RFID reads of the cabinet contents at different times (e.g., a read before the door release is activated and a read after the door release re-locks). In this manner, the cabinet controller could determine which items were removed from the cabinet during the period the door was open.

FIG. 20B illustrates a re-stock function. The function begins with the log in at step 350 and the selection of the re-stock function in step 351. Next, the user designates whether the re-stock will be of the cabinet or the cart. In other words, the cart may have also have a storage space which will hold implant components and instruments, but typically for a shorter time period than the cabinet. An item to be placed in the cabinet (or cart) will be scanned (in the bar code embodiment) in step 353, then placed in the item's proper shelf of bin in step 354, and then the process repeated for all items to be placed in the cabinet (or cart). The function terminates in step 356.

In a related embodiment, since the system computer communicates with the storage sensor and the deployment sensor, the system software may be configured to carry out the steps of: (i) recording a set of implant components departing the implant storage space; (ii) recording the set of implant components when detected by the deployment sensor; and then (iii) generating a restocking request listing the set of implant components departing the storage space. The set of implant components departing the storage space may be defined by a period of time. For example, the set may include those implant components (and/or instruments) which have departed the storage place over a given period of time, e.g., over the last 12 hours, 24 hours, or 72 hours. On the other hand, the system could define the set of implants as the group very recently removed from the storage space, e.g., the set of implant components departing the storage space over a period of no more than the last five minutes.

Figure 20C:
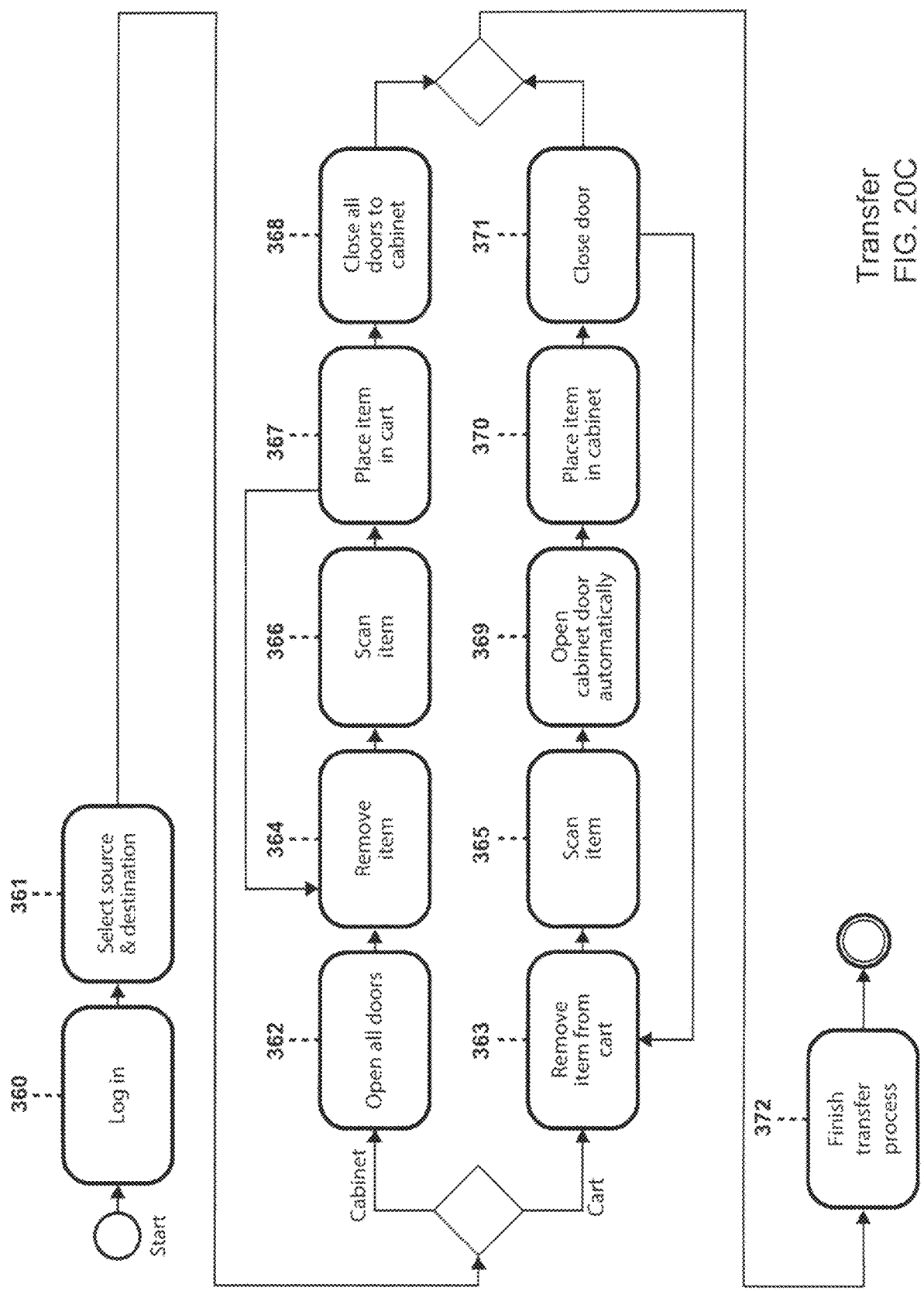

FIG. 20C illustrates a transfer function. After logging in (step 360), the user selects in step 361 the source and destination (cabinet or cart) of the item to be moved. Where the user selects transfer from cabinet to the cart, step 362 unlocks the cabinet door. In step 364, the item is removed from the cabinet, scanned in step 366, and placed in the cart in step 367. The process is repeated for all items to be transferred and the cabinet door is re-locked in step 368. If the user selects transfer from the cart to the cabinet, the user in step 363 removes the item from the cart and scans the item in step 365 with the cabinet scanner. After the cabinet controller receives the scan data, the controller releases the cabinet door lock in step 369. The user places the item on the proper shelf in the cabinet and steps 363 to 370 are repeated for all items to be transferred. Once no further scans are made during the transfer routine, the cabinet remains locked in step 371 and in step 372 the controller terminates the transfer routine.

Figure 21:
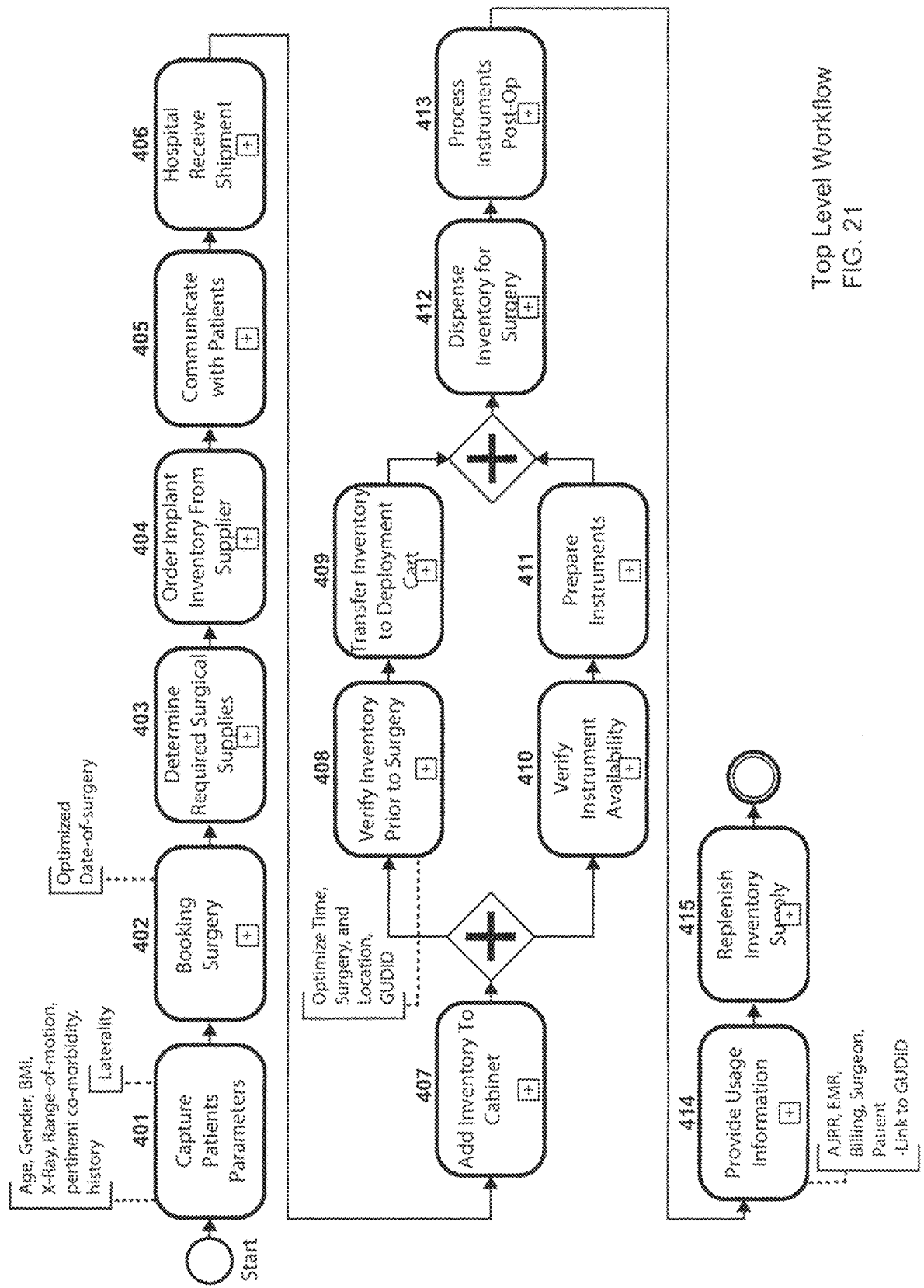
FIG. 21 is a high level flow chart illustrating certain embodiments of implant inventory control and implant deployment to an operating room.
Figure 22:
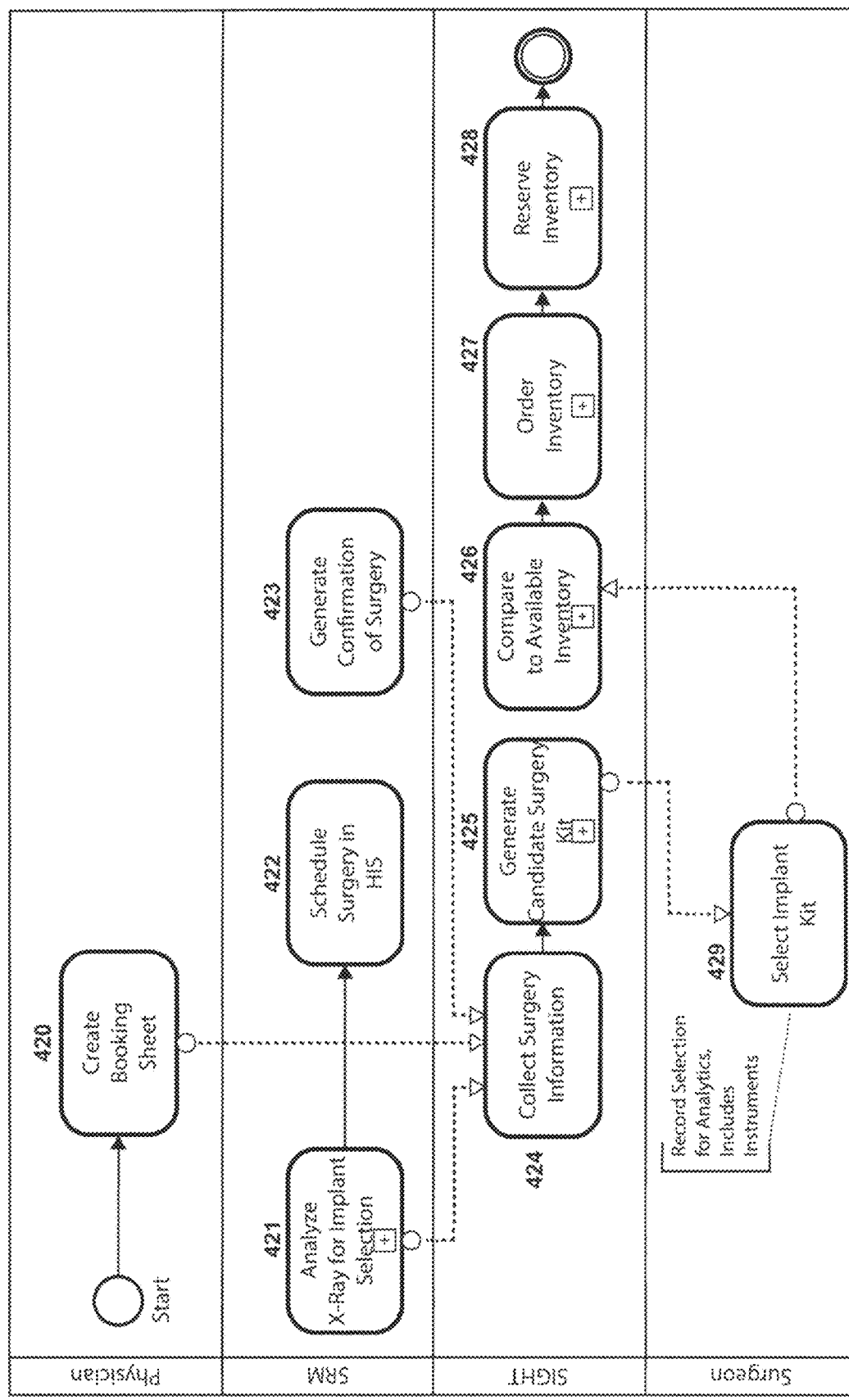
FIG. 22 is a flow chart illustrating one method embodiment for booking surgery.

In addition to the determination of a reduced set of implant components and instruments, certain embodiments of the present invention include methods of scheduling the implant surgery, confirming the required implant components and instruments are available, and replenishing inventory. FIG. 21 illustrates a top level workflow in one example embodiment. Beginning with step 401, the system captures necessary patient parameters. These patient parameters may include the patient metrics previously described (e.g., age, gender, BMI, range of motion, co-morbidity, medical history, etc.). Next in step 402, a surgery booking procedure is carried out as described in more detail in FIG. 22. Starting with step 420 in FIG. 22, the system prompts the patient's treating physician to create a booking sheet with information such as surgeon, hospital, date of surgery, name/age of patient, procedure type, instruments and implants required, insurance information, etc. In step 421, the appropriate surgical team member, for example the site readiness manager (SRM) under the supervision of the surgeon, determines the key anatomical features in the manner described above. In step 422, the SRM schedules the surgery into the hospital information system ("HIS"), typically reserving an operating room and other details required for scheduling the surgery. The SIGHT system in step 424 collects information from the booking sheet, the key anatomical points on the medical images, and confirmation of surgery scheduling (step 423). With this information, the system generates a suggested kit or reduced set of implant components and instruments, e.g., using the method previously described in FIGS. 12 to 16. In step 426, the surgeon confirms the reduced component and instruments set or makes edits to the same. In certain embodiments, the SIGHT system will record the surgeon's confirmation or selection of instruments and make the instrument selection the default setting for that surgeon and the particular implant procedure under consideration. Given the confirmed set of implant components and instruments, the SIGHT system in step 427 compares the required implant components and instruments to the inventory available in the relevant ODOC cabinet. If the inventory is not currently available in the ODOC cabinet, the SIGHT system places an order for the inventory in step 428 and finally, places a reservation (step 429) on the selected components and instrument until the scheduled day of surgery.

Figure 23:
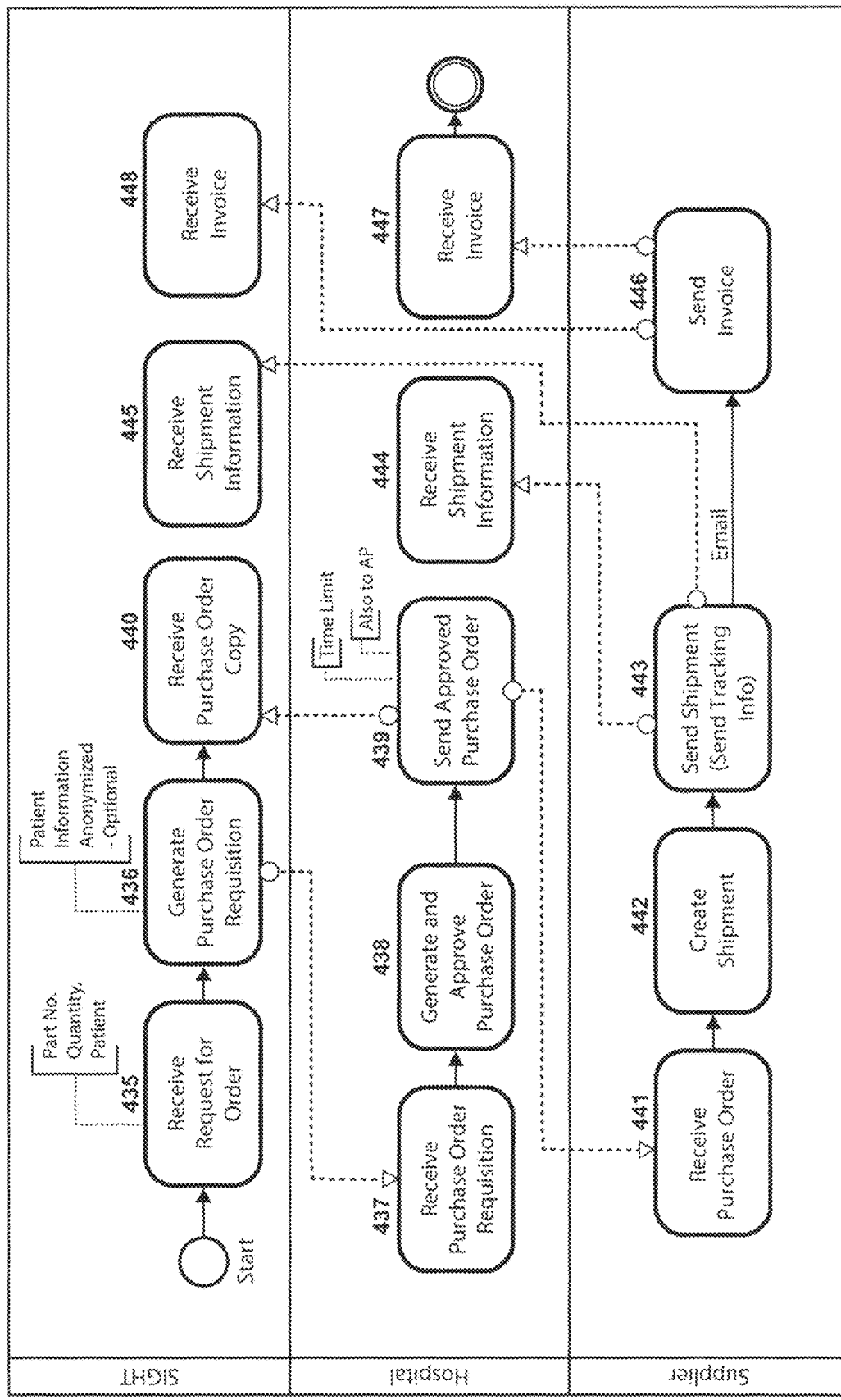
FIG. 23 is a flow chart illustrating one method embodiment for ordering implant inventory.

At step 403 in FIG. 21, the system returns a set of surgical supplies, e.g., sutures, scalpels, retractors, skin prep items, drapes, and similar general surgical supplies, based upon a database list associating such surgical supplies with the particular implant components and instruments selected. In step 404, the system may generate an order for implant inventory from a supplier as is necessary to maintain appropriate component and instrument levels in the ODOC cabinet. For example, in step 435 in FIG. 23, the SIGHT system may receive an order request initiated by the surgeon or SRM through the SIGHT system (e.g., step 429 in FIG. 22). In step 436, the SIGHT system generates a purchase order requisition which is received by the hospital system hosting the ODOC cabinet in step 437. The hospital system approves the purchase order in step 438 and transmits the purchase order to the implant supplier in step 439. At the supplier level, the purchase order is received, processed (a shipment created), and sent in steps 441 to 443, with the hospital and the SIGHT system receiving notice of the shipment in steps 444 and 445. The supplier invoices the hospital for the shipment in step 447 and provides the invoice information to the SIGHT system in step 448.

In FIG. 21, this embodiment of the SIGHT system shows the system communicating with patients in step 405 confirming date of surgery, giving pre-operative instructions, etc. The hospital will receive a shipment at step 406 and the inventory added to the ODOC cabinet at step 407. This step is described in more detail in FIG. 24, beginning with the receipt of the shipped inventory at the hospital in step 450. In step 451, the contents of the shipment is reconciled with the purchase order. This may be done for example, by the SRM bar code scanning inventory which has bar codes or in the case where the inventory has individualized RFID tags, bringing the inventory within the scanning radius of an RFID reader. In step 452, the destination for each item is determined, e.g., the SRM enters the specific ODOC cabinet in which the item is being stored. In step 454, the SIGHT system is given notice of the inventory being received at the hospital and the SIGHT system in step 455 receives the stock location (e.g., the specific ODOC cabinet) for each item of inventory. In step 453, the SRM loads the appropriate ODOC cabinet with the scheduled inventory items. Whether the SRM scans the inventory bar codes at the cabinet or a cabinet RFID reader detects RFID tags on the inventory items, the SIGHT system in step 456 may use this information to verify that the inventory items have been loaded in the ODOC cabinet.

Figure 24:
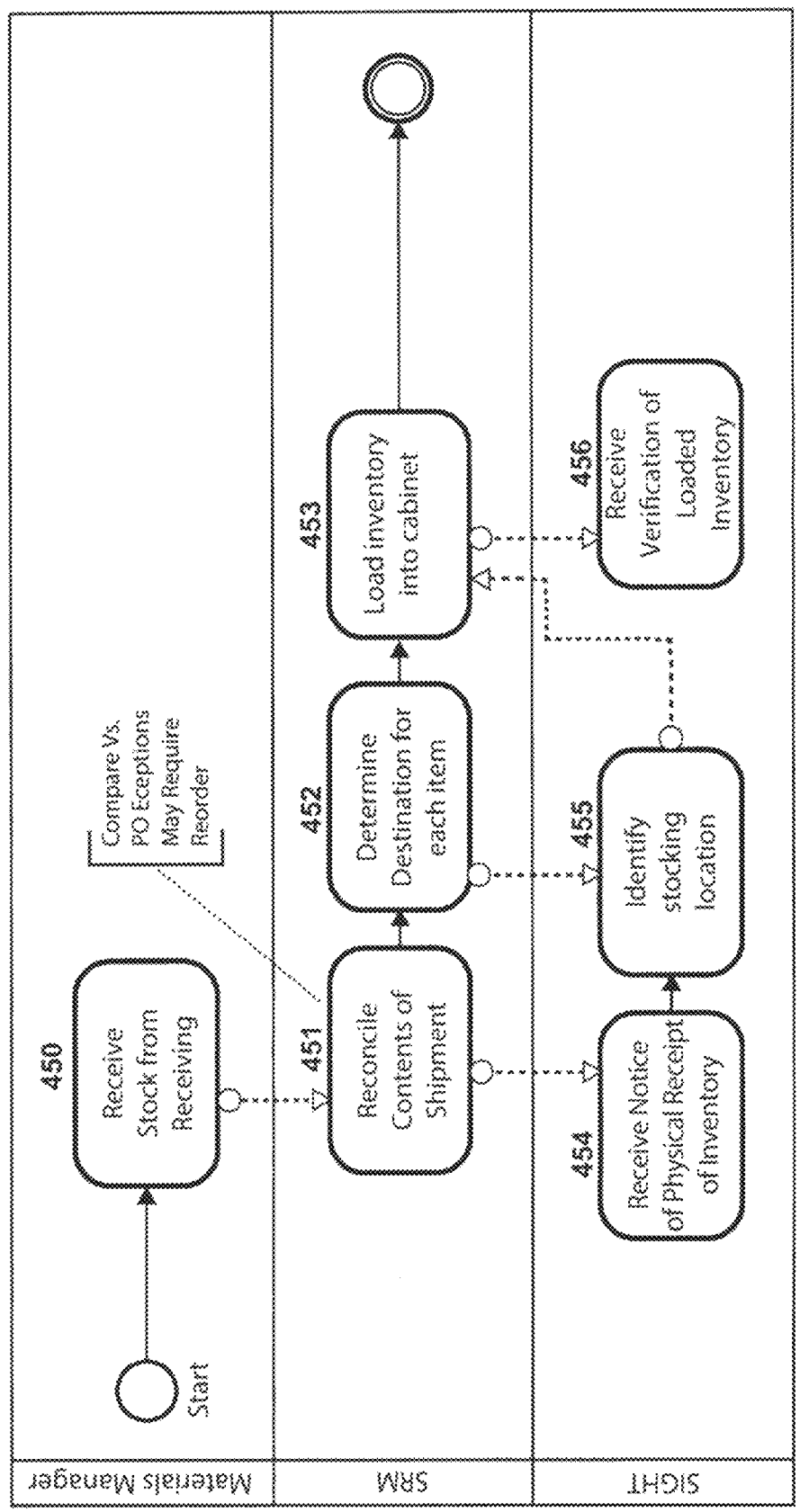
FIG. 24 is a flow chart illustrating one method embodiment for adding inventory to an implant cabinet.
Figure 25:
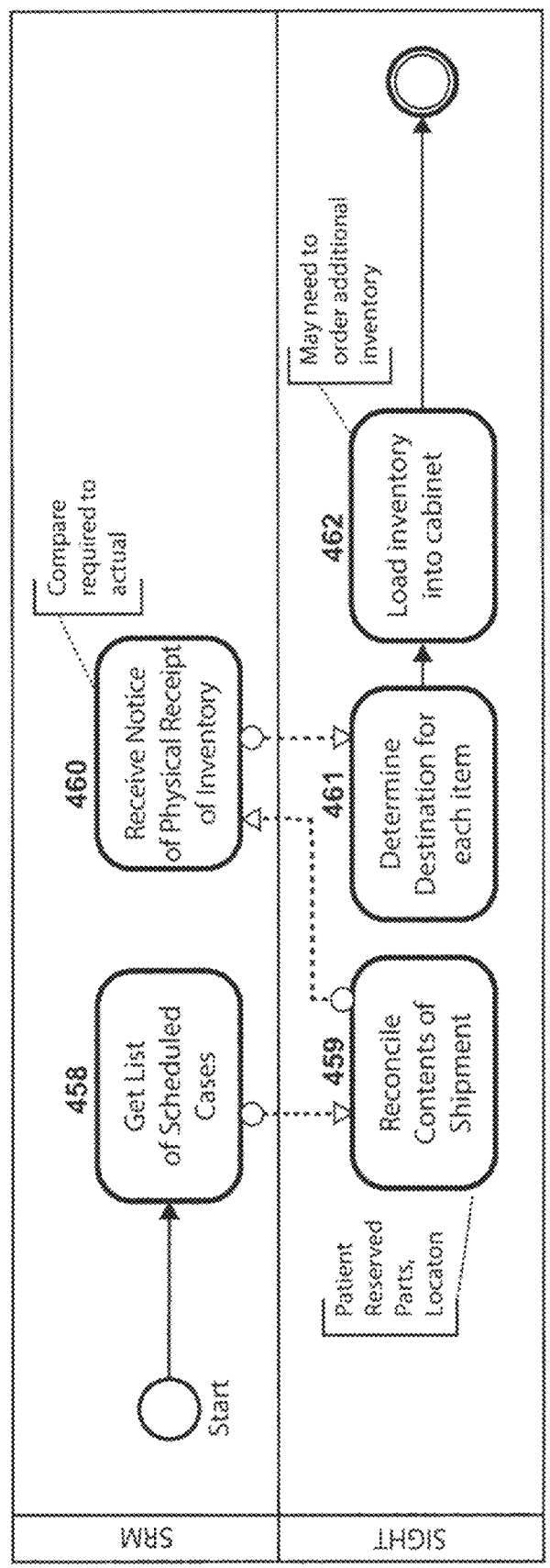
FIG. 25 is a flow chart illustrating one method embodiment for verifying implant inventory.

FIG. 21, step 408 verifies the availability of consumable inventory (i.e., implant components) prior to surgery, with one specific procedure seen in FIG. 24. In FIG. 25 step 458, the SRM transmits to the SIGHT system the list of scheduled cases and the SIGHT system in turn provides the scheduled cases and corresponding implant components required (i.e., as determined previously in the selection procedure of FIGS. 12-16). In step 460, the SRM confirms that the required implant components are available, e.g., (i.e., are located in the ODOC cabinet at the hospital in question. Whether or not the implant components are in physical inventory is transmitted to the SIGHT system in step 461 and step 462 reconciles the results of the physical inventory check with the implant components required in the procedure. If the necessary implant components are not available at the hospital in question, the SIGHT system will order the needed additional inventory (e.g., see FIG. 23 for ordering implant inventory). In certain embodiments, if the required inventory cannot be obtained or other necessary requirements for surgery are missing or not confirmed in the system (e.g., required test results or acceptable payment/reimbursement information), then the system generates and sends notices of the missing/unconfirmed requirements to relevant entities, e.g., the surgeon, the hospital, the patient, etc. so that the requirements may be fulfilled or the surgery re-scheduled.

Thus, the above system provides another method embodiment for managing implants. The system includes (i) an implant storage space, (ii) a storage sensor located proximate the storage space, the storage sensor configured to detect implant components, and (iii) a system computer communicating with the storage sensor. The method involves first determining a set of implant components scheduled to depart the storage space; then removing from the storage space the set of implant components scheduled to depart the storage space; and finally, operating the storage sensor to communicate to the computer system that the set of implant components have been removed from the storage space.

In FIG. 21, step 409, the implant components are transferred to the deployment cart (i.e., cart 330 above) as described in more detail in FIG. 26. In step 465, the SRM requests a schedule of cases (typically for a particular day, but possibly for a longer period of time) from both the SIGHT system and the hospital electronic medical records (emr) and the SRM in step 468 reconciles any differences in the scheduling, either manually or automatically using appropriate scheduling software. With the confirmed cases, a "pick list" of required implant components is generated for each case along with the particular ODOC cabinets (if more than one on site) from which the implant components are to be withdrawn. Steps 471 and 472 address the SRM withdrawing the implant components from the cabinet and adding them to the cart (which is described in more detail above in reference to FIG. 20C). In the typical case, prior to the cart being wheeled to the operating room (i.e., the cart's scheduled destination) as per step 473, implant instruments and surgical instruments will be added to the cart in accordance with steps 410 and 411 in FIG. 21.

Step 410's verification of instrument (i.e., implant instruments and surgical instruments) availability is described in more detail in FIG. 27, steps 490 to 492. In step 490, the SRM selects the list of scheduled cases, which includes the surgeon name, from which the SIGHT system may access the previously stored surgeon profile. In step 491 the SIGHT system provides a suggested set of implant instruments and surgical instruments based on a reduction process such as described above in reference to FIGS. 12 to 16. In step 492, the SRM (or the implanting surgeon) confirms whether he or she wishes to utilize the instrument set suggested by the SIGHT system or modify any particulars of the instrument set. Next in step 493, the instruments are assembled into one or more trays and then sterilized in step 494. The assembly of the trays in step 493 may include ordering the instruments in the trays. Alternatively, the instruments may be placed in the trays in an unordered fashion, to be place in order after the trays have reached the OR. Step 495 involves the inclusion of a series of instrument images and written instructions indicating the order in which the instruments are to be laid out and utilized in the OR, e.g., similar to the images and description seen in FIGS. 15C and 15D. Next the tray(s) of instruments will be place on a deployment cart 330 in step 496 (which may be the same or a different cart from the one carrying the implant components). Step 497 involves the scanning of the label on the tray by the cart scanner, thereby confirming (in step 498) that the tray has been placed on the cart. After the cart is wheeled to the OR and the tray(s) removed from the cart (steps 499 and 500), there is another scan of the tray(s) by either a scanner on the cart or a separate scanner in the OR which confirms to the local SIGHT server that the tray(s) have reached the OR. In the case of the scanner on the cart, the cart's location in the OR is sent with confirmation that the tray(s) have been read by the scanner. Step 502 again confirms that the tray(s) reaching the OR match the particular patient schedule for surgery at that time and in that OR. Typically upon arrival of the tray(s), the instruments will be laid out on a surgical table (or "back table") located in the OR. In step 503, a scrub tech or other OR personnel can confirm the instrument layout matches that shown in the images and written materials included in step 495.

Since the system computer is communicating with the storage sensor (e.g., bar code scanner at storage cabinet) and the deployment sensor (e.g., bar code scanner at the cart), the system may carry out a series of steps such as (i) receiving data representing a set of implant components scheduled to depart the implant storage space; (ii) receiving data indicating that the storage sensor has detected the set of implant components; and then (iii) receiving data indicating that the deployment sensor has detected the set of implant components at a scheduled destination. In this example, the "schedule destination" may be the OR (as suggested in step 473 of FIG. 26). In certain embodiments, the cart may include a "locator device" or a method by which the system can determine the approximate location of the cart. The locator device may be GPS or it may be a device that triangulates RF signals sent or received by the cart. This would allow the system to determine when the cart has reached the OR or another scheduled destination.

In FIG. 21, step 412, the system dispenses or deploys the inventory during surgery as described in more detail in FIG. 28. In FIG. 28, step 510, the surgeon, who at this stage has exposed and directly measured the patient's femur, now makes a decision on which femoral component trial size to utilize. It will be remember that the implant component/ instrument reduction process in FIGS. 12 to 16 contemplates a predicted size of implant components/instruments and the sizes immediately above and below the predicted size. Once a femoral component trial size is selected, the system in step 511 will suggest compatible trials for the tibial component and patellar component using manufacturer information concerning which tibial component and patellar component are compatible with the selected femoral component. In steps 512 and 513, the surgeon makes his or her choice of tibial baseplate and insert trials and that decision is entered into the system. In step 514, the SIGHT system indicates whether (based upon manufacturer information) the selected tibial insert trials are compatible with other components selected by the surgeon. In step 515, the surgeon makes the final determination on the compatibility of the trials and other components. In step 516, the surgeon verifies all selected trials by assembly on the patient's prepared femur and tibia and performing a trail reduction range of motion. Based on the verified trials, the corresponding implant components are identified in step 517 and this information is entered into the SIGHT system by a "circulator" or other OR personnel outside the sterile field in step 518. Typically this individual will next withdraw from the cart the appropriate boxes containing the implant components in step 519 and in step 520, these boxes of implants are again scanned to maintain a record of which implants components were taken from the cart for ultimate implantation in the patient. In step 521, the SIGHT system confirms that the implant components just scanned correspond with the trials which were identified in step 518. Finally, the box is opened in step 522 and in step 523 the appropriate OR personnel is requested to identify whether components from open boxes are actually implanted into a patient or become wasted parts (e.g., the implant component box was inadvertently opened or that particular implant component must be rejected for reasons such as being contaminated prior to implantation). Finally, step 524 directs all unused cart inventory be returned to stock status for future use.

Returning to FIG. 21, after the instruments are deployed for surgery in step 412, the instruments are processed post-operatively in step 413 as illustrated in more detail in FIG. 29. First the instruments are returned to their originating tray in step 530. Next the instruments are transported to the hospital's central sterilization facility and cleaned in steps 531 and 532. In steps 533 the SRM confirms no instruments are missing and that all appear in working order. The SRM then restocks the instruments, replacing any that are missing or damaged, and scans the bar codes on the instruments in step 534. Alternatively, and particularly with instruments too small to carry a bar code or RFID tag, the system could use a computer vision system to identify instruments to be restocked (or otherwise being tracked within the SIGHT system). With the SIGHT system receiving the scanned bar codes, the system may update its instrument inventory list in step 535. In FIG. 21, step 414, the SIGHT is able to generate reports on usage, such as implant sizes utilized, time of instrument usage in OR, surgeon instrument preferences, etc. In step 415, the SIGHT system will replenish inventory supply to a level necessary to accommodate the expected use through a specified period of time, i.e., with the inventory order method similar to that described in FIG. 23. In certain embodiments, the system determines an implant components expiration date (e.g., either from prompting the SRM to enter that date or obtaining the date from manufacturer codes). The system can then give notice when the implant component needs to be replace in inventory due to reaching its expiration date. Similarly, where sterilized implant instruments and surgical instruments should be used within a given time period of their latest sterilization, the system can give notices when the sterilization time period has expired based upon when the instruments were loaded in to the ODOC cabinet.

Although the inventive concept has been described in terms of certain specific examples, many obvious variations and alternatives will be apparent to those skilled in the art. For example, in one embodiment of this invention, all of the surgical instruments, implant instruments, and implant componentss are marked for easy identification with bar codes or radio frequency identification tags to ensure the correct instrument or component is selected to be transported to the operating room and selected at the proper time during the surgery based upon the determinations made as part of this invention.

In another embodiment of this invention, all of the surgical instruments, implant instruments, and implant components could be affirmatively identified using a camera or vision sensor which is interfaced to a computer with a database of visual images of such surgical instruments and components to positively identify each instrument or component is selected to be transported to the operating room and selected at the proper time during the surgery based upon the determinations made as part of this invention.

A further embodiment is a method of assisting an orthopedic implant procedure in an operating room with an instrument table. The method involves printing on a flexible media a sub-set of surgical instruments and implant instruments arranged into a substantially specific order based upon a determination of a sequence of bone cuts to be performed in the procedure. The flexible media may be a paper, plastic, or clothe (e.g., a surgical drape). The flexible media is placed on the instrument table, and then OR personnel may arrange the surgical instruments and implant instruments based on the order shown on the flexible media.

Another method embodiment is assisting an orthopedic implant procedure in an operating room takes place in an environment where there is (i) a surgical table in the operating room, (ii) a camera viewing the surgical table, and (iii) a computer receiving images from the camera. The method loads into memory of the computer a sub-set of surgical instruments and implant instruments arranged into a substantially specific order. OR personnel place the sub-set of surgical instruments and implant instruments on the surgical table. The computer captures an image with the camera of the surgical instruments and implant instruments on the surgical table, and then determines which of the surgical instruments and implant instruments loaded into the computer memory are present in the image of surgical instruments and implant instruments.

All such variations and alternatives should be considered part of the present invention and to fall within the scope of the below claims.

The invention claimed is:

1. A method of assisting an orthopedic implant procedure in an operating room with a display communicating with a computer system, the method comprising the steps of:
   a. loading on the computer system a sub-set of surgical instruments and implant instruments arranged into a substantially specific order based upon a determination of a sequence of bone cuts to be performed in the procedure;
   b. presenting on the display images of the surgical instruments and implant instruments in the substantially specific order;
   c. on the display, advancing through the substantially specific order of the surgical instruments and implant instruments;
   d. wherein a user interface to the computer system is located in the operating room and the user interface allows a user to control the computer system's advancement though the substantially specific order on the display;
   e. providing (i) a surgical table in the operating room, (ii) a camera viewing the surgical table, and (iii) the computer system receiving images from the camera;
   f. loading into memory of the computer system a sub-set of surgical instruments and implant instruments arranged into a substantially specific order;
   g. placing the sub-set of surgical instruments and implant instruments on the surgical table;
   h. capturing an image with the camera of the surgical instruments and implant instruments on the surgical table; and
   i. determining which of the surgical instruments and implant instruments loaded into the computer memory are present in the image of surgical instruments and implant instruments.

2. The method of claim 1, wherein the surgical instruments are bone cutting/alignment instruments.

3. The method of claim 1 wherein the surgical instruments and implant instruments are presented on the display in separate groups associated with discrete steps in the implant procedure.

4. The method of claim 3 wherein the discrete steps in the implant procedure are from the group consisting of: (i) Femoral Alignment, (ii) Distal Femoral Cut, (iii) Tibial Alignment, (iv) Proximal Tibial Cut, (v) Extension Gap Confirmation, (vi) Femoral Comp Sizing/Positioning, (vii) Anterior Femoral Cut, (viii) Posterior Femoral Cut, (ix) Flexion Gap Confirmation, (x) Anterior Chamfer Femoral Cut, (xi) Posterior Chamfer Femoral Cut, (xii) Patella Resurfacing Cut, (xiii) Femoral Comp Finishing, (xiv) Femoral Comp Trialing, (xv) Tibial Baseplate & Insert Trialing, (xvi) Patella Comp Finishing, (xvii) Patellar Comp Trialing, (xviii) ROM - Trial Reduction, (xix) Tibial Baseplate Finishing, (xx) Femoral Comp Fixation, (xxi) Tibial Baseplate Fixation, (xxii) Patellar Comp Fixation, (xxiii) Tibial Insert Insertion.

5. The method of claim 1, wherein the set of implant instruments include at least one from the group consisting of a femoral drill guide, a femoral trial, a tibial baseplate trial, a tibial insert trail, and a patellar drill guide.

6. The method of claim 5, wherein the set of surgical instruments includes at least one from the group consisting of a femoral IM cutting guide, a femoral alignment guide, a tibial IM alignment guide, a tibial cutting guide, a patellar caliper, a patellar resection guide, and an implant impactor.

7. The method of claim 1 further comprising the step of generating a visual list of the surgical instruments in the substantially specific order.

* * * * *